(12) United States Patent
Zergiebel et al.

(10) Patent No.: US 11,786,244 B2
(45) Date of Patent: Oct. 17, 2023

(54) MANUAL RETRACTION TOOL FOR USE WITH AN ELECTROMECHANICAL SURGICAL DEVICE

(71) Applicant: Covidien LP, Mansfield, MA (US)

(72) Inventors: Earl Zergiebel, Guilford, CT (US); Pawel Abramek, Berlin, CT (US)

(73) Assignee: Covidien LP, Mansfield, MA (US)

( * ) Notice: Subject to any disclaimer, the term of this patent is extended or adjusted under 35 U.S.C. 154(b) by 22 days.

(21) Appl. No.: 17/349,968

(22) Filed: Jun. 17, 2021

(65) Prior Publication Data
US 2021/0307747 A1  Oct. 7, 2021

Related U.S. Application Data

(60) Division of application No. 15/887,229, filed on Feb. 2, 2018, now Pat. No. 11,039,833, which is a
(Continued)

(51) Int. Cl.
*A61B 17/00* (2006.01)
*A61B 17/072* (2006.01)
(Continued)

(52) U.S. Cl.
CPC ............ *A61B 17/072* (2013.01); *A61B 17/00* (2013.01); *A61B 17/07207* (2013.01); *A61B 17/1155* (2013.01); *A61B 17/2909* (2013.01); *A61B 2017/00017* (2013.01); *A61B 2017/0042* (2013.01); *A61B 2017/0046* (2013.01); *A61B 2017/00336* (2013.01);
(Continued)

(58) Field of Classification Search
None
See application file for complete search history.

(56) References Cited

U.S. PATENT DOCUMENTS

| 5,547,117 | A | 8/1996 | Hamblin et al. |
| 7,044,353 | B2 | 5/2006 | Mastri et al. |

(Continued)

FOREIGN PATENT DOCUMENTS

| WO | 2009039506 A1 | 3/2009 |
| WO | 2009/088507 A1 | 7/2009 |

OTHER PUBLICATIONS

U.S. Appl. No. 61/911,774, filed Dec. 4, 2013.
(Continued)

*Primary Examiner* — Erica S Lee
(74) *Attorney, Agent, or Firm* — CARTER, DELUCA & FARRELL LLP

(57) ABSTRACT

A manual retraction tool for use with a surgical tool assembly of a surgical device includes a shaft, a rotation mechanism, and a trigger. The shaft is dimensioned to be inserted into a rotational connector of a surgical tool assembly and to effect rotation of the connector upon rotation of the shaft. The rotation mechanism configured to rotatably support the shaft. The trigger is operably connected to the rotation mechanism such that when the trigger is actuated from a first position to a second position, the rotation mechanism rotates the shaft about a longitudinal axis in a first direction to effect rotation of the rotational connector of the surgical tool assembly.

9 Claims, 16 Drawing Sheets

Related U.S. Application Data continuation-in-part of application No. 15/586,353, filed on May 4, 2017, now Pat. No. 10,617,486.

(60) Provisional application No. 62/331,796, filed on May 4, 2016.

(51) Int. Cl.
*A61B 17/29* (2006.01)
*A61B 17/115* (2006.01)
*A61B 90/00* (2016.01)

(52) U.S. Cl.
CPC ............... *A61B 2017/00367* (2013.01); *A61B 2017/00393* (2013.01); *A61B 2017/00398* (2013.01); *A61B 2017/00407* (2013.01); *A61B 2017/00473* (2013.01); *A61B 2017/2923* (2013.01); *A61B 2090/031* (2016.02)

(56) References Cited

U.S. PATENT DOCUMENTS

| | | | |
|---|---|---|---|
| 7,143,926 | B2 | 12/2006 | Shelton, IV et al. |
| 7,364,061 | B2 | 4/2008 | Swayze et al. |
| 7,490,749 | B2 | 2/2009 | Schall et al. |
| 7,588,175 | B2 | 9/2009 | Timm et al. |
| 7,819,296 | B2 | 10/2010 | Hueil et al. |
| 7,819,896 | B2 | 10/2010 | Racenet |
| 8,006,885 | B2 | 8/2011 | Marczyk |
| 8,011,551 | B2 | 9/2011 | Marczyk et al. |
| 8,056,787 | B2 | 11/2011 | Boudreaux et al. |
| 8,074,858 | B2 | 12/2011 | Marczyk |
| 8,210,412 | B2 | 7/2012 | Marczyk |
| 8,608,045 | B2 | 12/2013 | Smith et al. |
| 9,597,104 | B2 | 3/2017 | Nicholas et al. |
| 10,588,629 | B2 | 3/2020 | Malinouskas et al. |
| 10,751,058 | B2 | 8/2020 | Cabrera et al. |
| 11,039,833 | B2 | 6/2021 | Zergiebel et al. |
| 2009/0314821 | A1 | 12/2009 | Racenet |
| 2010/0089970 | A1 | 4/2010 | Smith et al. |
| 2011/0000025 | A1 | 1/2011 | Johnson et al. |
| 2011/0121049 | A1 | 5/2011 | Malinouskas et al. |
| 2011/0125138 | A1 | 5/2011 | Malinouskas et al. |
| 2012/0116390 | A1 | 5/2012 | Madan |
| 2012/0241494 | A1 | 9/2012 | Marczyk |
| 2013/0324978 | A1 | 12/2013 | Nicholas et al. |
| 2013/0324999 | A1 | 12/2013 | Price et al. |
| 2014/0001235 | A1 | 1/2014 | Shelton, IV |
| 2014/0090522 | A1 | 4/2014 | Huang |
| 2014/0171923 | A1* | 6/2014 | Aranyi .................. A61B 17/00 606/1 |
| 2015/0053737 | A1 | 2/2015 | Leimbach |
| 2015/0076205 | A1* | 3/2015 | Zergiebel ......... A61B 17/07207 227/175.1 |
| 2015/0297205 | A1 | 10/2015 | Zergiebel et al. |
| 2017/0319287 | A1 | 11/2017 | Zergiebel et al. |

OTHER PUBLICATIONS

Partial European Search Report corresponding to counterpart application EP 14 19 9662.9 dated Sep. 14, 2015.
Extended European Search Report corresponding to counterpart Int'l Appln. No. EP 14199662.9, dated Jan. 13, 2016.
European Search Report dated Sep. 23, 2019 corresponding to counterpart Patent Application EP 19154702.5.
Partial European Search Report dated Jun. 14, 2019 corresponding to counterpart Patent Application EP 19154702.5.

* cited by examiner

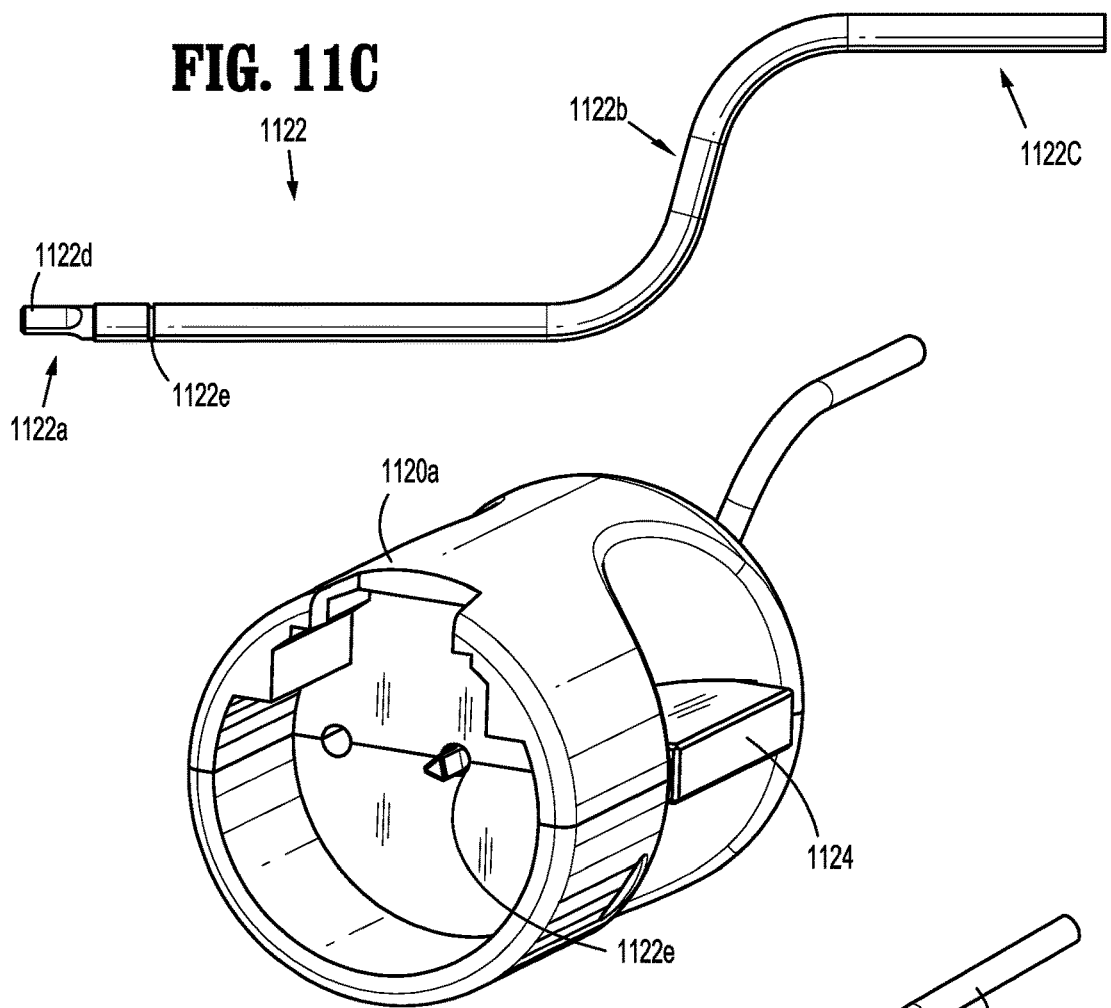
FIG. 11C
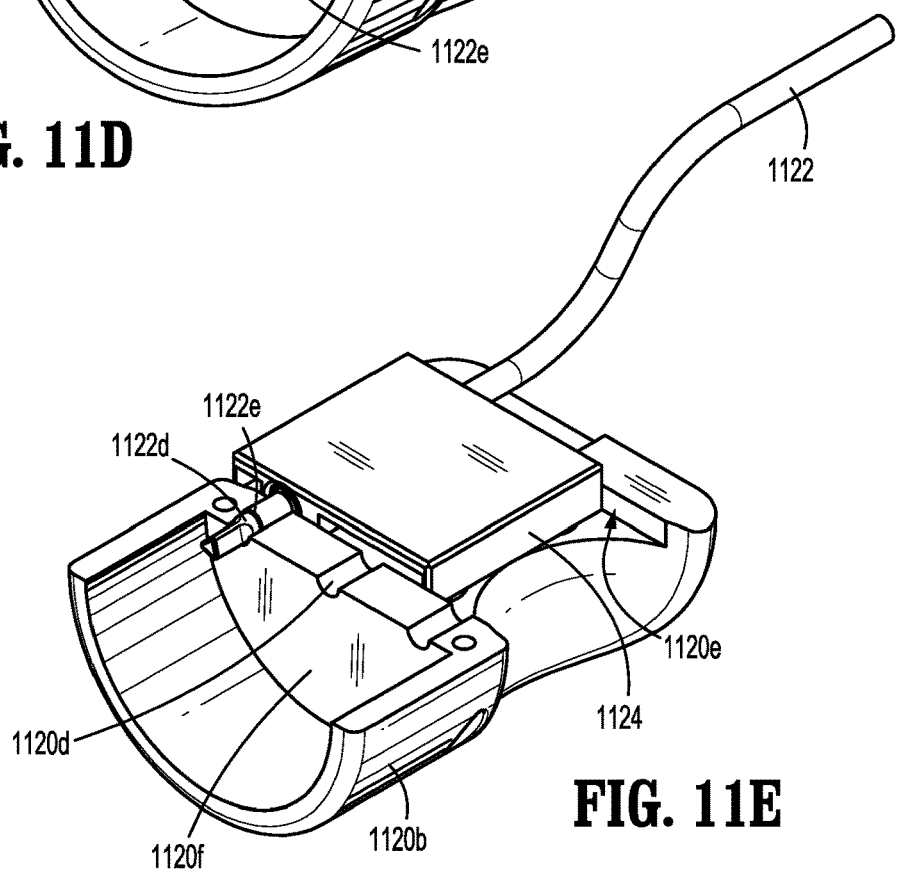
FIG. 11D
FIG. 11E

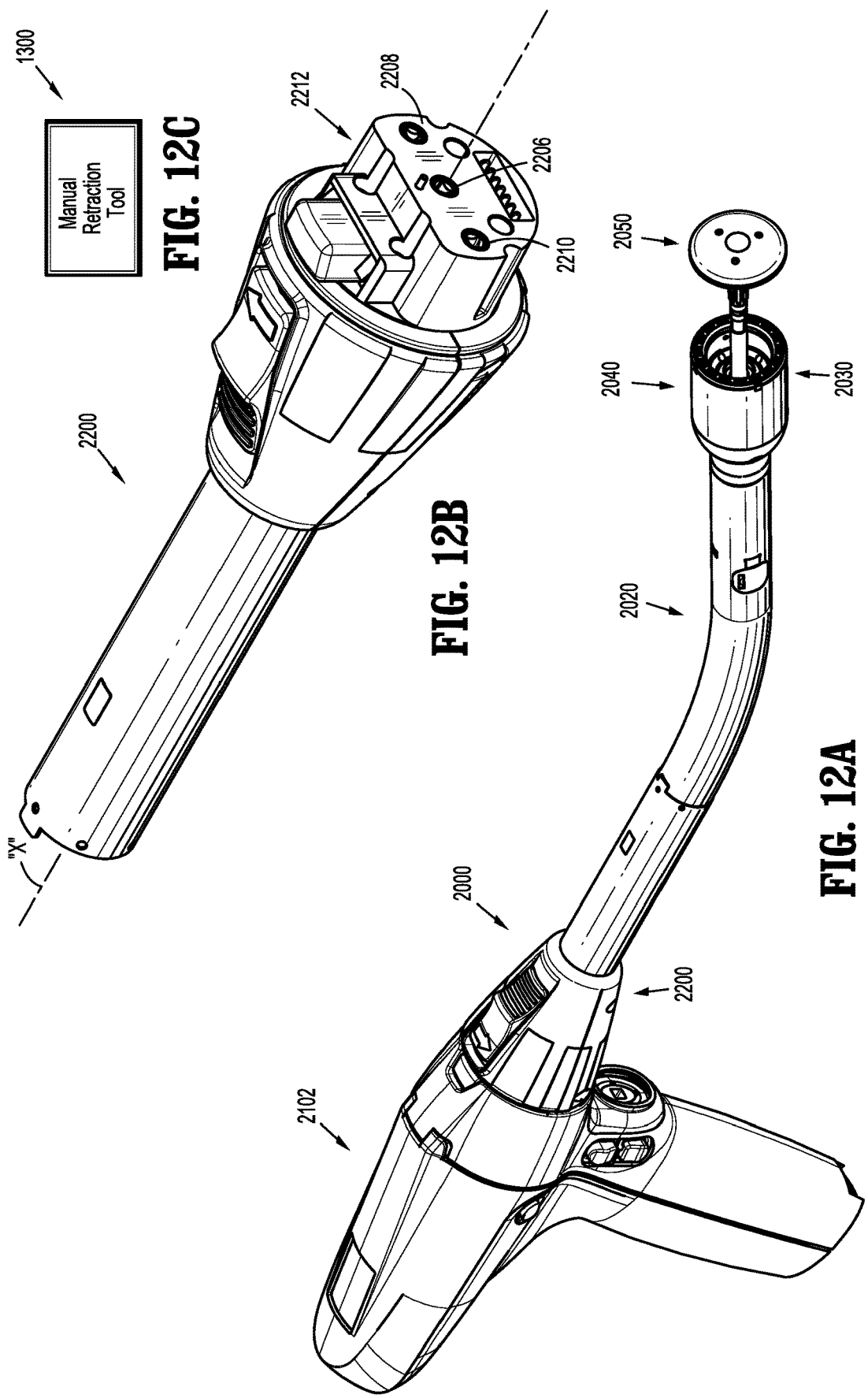

MANUAL RETRACTION TOOL FOR USE WITH AN ELECTROMECHANICAL SURGICAL DEVICE

CROSS-REFERENCE TO RELATED APPLICATIONS

This application is a Divisional Application of U.S. patent application Ser. No. 15/887,229, filed on Feb. 2, 2018, now U.S. Pat. No. 11,039,833, which is a Continuation-in-Part Application of U.S. patent application Ser. No. 15/586,353, filed on May 4, 2017, now U.S. Pat. No. 10,617,486, which claims the benefit of and priority to U.S. Provisional Patent Application Ser. No. 62/331,796 filed May 4, 2016, the entire disclosures of which are incorporated by reference herein.

BACKGROUND OF RELATED ART

The present disclosure relates to surgical apparatus, devices and/or systems for performing endoscopic surgical procedures. More specifically, the present disclosure relates to manual retraction tools configured for use with electromechanical, hand-held surgical apparatus, to kits, and methods of use thereof.

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or, in some instances, sterilized for re-use.

In certain instances, an adapter assembly is used to interconnect an electromechanical surgical device with an end effector, e.g., any one of a number of surgical loading units, to establish a mechanical and/or electrical connection therebetween. The adapter assembly, or different adapter assemblies, may be attached and detached to an electromechanical surgical device during a surgical procedure.

These electromechanical surgical devices offer some advantages over purely mechanical devices.

SUMMARY

The present disclosure is directed to a manual retraction tool that can be used in lieu of a surgical device of an electromechanical surgical device to provide a clinician with a means to manually operate and perform standard operations of an end effector associated with the surgical device, for example, to complete or reverse actuation, articulation, and/or rotation functions of the end effector.

In one aspect of the present disclosure, a manual retraction tool is configured for use with a surgical tool assembly of a surgical device, the manual retraction tool including: a shaft extending between a distal tip and a proximal tip, each of the distal and the proximal tips dimensioned to be inserted into a rotational connector of a surgical tool assembly and to effect rotation of the connector upon rotation of the shaft; a rotation mechanism configured to rotatably support the shaft; and a trigger operably connected to the rotation mechanism such that when the trigger is actuated from a first position to a second position, the rotation mechanism rotates the shaft about a longitudinal axis in a first direction to effect rotation of the rotational connector of the surgical tool assembly.

In embodiments, the rotation mechanism includes a nut defining a threaded through-hole configured to rotatably support a threaded portion of the shaft, wherein when the trigger is actuated from the first position to the second position, the threaded through-hole of the nut engages the threaded portion of the shaft to rotate the shaft about the longitudinal axis.

In embodiments, the manual retraction tool further includes a ratchet assembly having a ratchet wheel and biasing member, the ratchet wheel defining a through-hole fixedly supporting the shaft and the biasing member configured to engage the ratchet wheel such that the shaft is restricted from rotating about the longitudinal axis in a second direction opposite the first direction when the trigger returns from the second position to the first position.

In embodiments, the shaft includes a distal shaft and a proximal shaft, wherein the rotation mechanism includes a gear assembly having a first gear operatively coupled to a second gear, wherein the first gear engages the trigger and the second gear fixedly supports the proximal shaft such that actuation of the trigger from the first position to the second position engages the first gear and in turn engages the second gear to rotate the proximal shaft about the longitudinal axis in the first direction.

In embodiments, the shaft includes a distal shaft and a proximal shaft, wherein the ratchet assembly includes a ratchet wheel fixed to the distal shaft and a clutch slidably located on the proximal shaft, the ratchet wheel having a plurality of grooves and the clutch having a plurality of teeth configured to operatively engage the plurality of grooves of the ratchet wheel, wherein when the proximal shaft rotates about the longitudinal axis in the second direction, the engagement between the clutch and the ratchet wheel prevents the distal shaft from rotating about the longitudinal axis in a second direction opposite the first direction when the trigger returns from the second position to the first position.

In embodiments, each tooth of the plurality of teeth of the clutch includes a flat portion and an angled portion and each groove of the plurality of grooves of the ratchet wheel includes a flat portion and an angled portion, wherein when the proximal shaft rotates about the longitudinal axis in the first direction, the flat portions of the plurality of teeth engage the flat portions of the plurality of grooves such that the distal shaft rotates about the longitudinal axis in the first direction, and when the proximal shaft rotates about the longitudinal axis in the second direction, the angled portions of the plurality of teeth engage the angled portions of the plurality of grooves such that the distal shaft is restricted from rotating about the longitudinal axis in the second direction.

In embodiments, the manual retraction tool further includes, a linkage assembly operably coupling the trigger and the rotation mechanism, the linkage assembly having a first link and a second link, the first link being coupled to the nut and the second link being coupled to the housing, wherein when the trigger is actuated from the first position to the second position, the first link drives the nut along the longitudinal axis to effect rotation of the shaft about the longitudinal axis in a first direction.

In another aspect of the present disclosure, a manual retraction tool is configured for use with a surgical tool assembly of a surgical device, the manual retraction tool including: a housing; and a shaft assembly at least partially supported in the housing and dimensioned to be inserted into a rotational connector of a surgical tool assembly, the shaft assembly including a distal shaft operably coupled to a proximal shaft, wherein the shaft assembly is configured to effect rotation of the rotational connector of the surgical tool assembly upon rotation of the proximal shaft about a longitudinal axis.

In embodiments, the distal shaft includes a gear rotatably coupled to a gear extending from the proximal shaft such that rotation of the proximal shaft about the longitudinal axis in a first direction effects rotation of the distal shaft in a second opposite direction.

In another aspect of the present disclosure, a manual retraction tool is configured for use with a surgical tool assembly of a surgical device, the manual retraction tool including: a housing; a shaft at least partially supported in the housing and dimensioned to be inserted into a rotational connector of a surgical tool assembly, the shaft being configured to effect rotation of the rotational connector upon rotation of the shaft about a longitudinal axis; a ratchet assembly including a rack and a ratchet wheel, the ratchet wheel being supported on the shaft such that engagement between the rack and the ratchet wheel effects rotation of the shaft about a longitudinal axis; and a trigger operably connected to the ratchet assembly such that when the trigger is actuated from a first position to a second position, the ratchet assembly rotates the shaft about a longitudinal axis in a first direction to effect rotation of the rotational connector of the surgical tool assembly.

In embodiments, the trigger is operably coupled to a biasing member configured to urge the trigger to the first position.

In embodiments, the ratchet assembly further includes a first biasing member and a second biasing member, the first biasing member configured to resist rotation of the ratchet wheel about the longitudinal axis with respect to the rack in a second direction, and the second biasing member configured to urge the rack into engagement with the ratchet wheel, wherein when the trigger is actuated from the first position to the second position, the rack engages the ratchet wheel to effect rotation of the ratchet wheel in the first direction.

In embodiments, the ratchet assembly includes a shelf rotatably located adjacent the rack, the shelf being resiliently biased to engage the rack, to space apart the rack and the ratchet wheel, when the trigger is in the first position such that translation of the rack does not effect rotation of the ratchet wheel.

In embodiments, the trigger includes an arm being configured to engage the shelf, wherein when the trigger is in the second position, the arm engages the shelf, to space apart the shelf and the rack, to effect rotation of the ratchet wheel in the first direction when the rack translate transversely with respect to the longitudinal axis.

In embodiments, the housing includes an internal structure configured for supporting the rack and effecting engagement between the rack and the ratchet wheel as the rack translates along the internal structure transversely with respect to the longitudinal axis.

In embodiments, the rack translates along the internal structure for a distance equal to a length of the internal structure when the trigger is actuated from the first position to the second position.

In another aspect of the present disclosure, a manual retraction tool is configured for use with a surgical tool assembly of a surgical device, the manual retraction tool including: a housing configured for releasable attachment to a surgical tool assembly, the housing including a first through-hole and a second through-hole configured for alignment with a rotational connector of a surgical tool assembly; and a crank at least partially supported in the housing and dimensioned to be inserted into the rotational connector of the surgical tool assembly, the crank being configured to effect rotation of the rotational connector upon rotation of the crank about a longitudinal axis.

In embodiments, the manual retraction tool further includes a slider disposed within a track defined in the housing, the slider configured to support a distal portion of the crank and translate along the track of the housing to locate the distal portion of the crank from the first through-hole to the second through-hole of the housing and vice-versa.

In embodiments, the slider includes a through-hole configured for locating the distal portion of the crank, the through-hole further including a biasing member resiliently biased to urge the crank in a distal direction.

In another aspect of the present disclosure, a kit including a manual retraction tool for use with a surgical tool assembly of a surgical device includes, a first electromechanical surgical device having a first adapter assembly configured for selective connection with a first end effector, a second electromechanical surgical device having a second adapter assembly configured for selective connection with a second end effector, a handle housing configured for selective connection with the first and second adapter assemblies, and a manual retraction tool configured for selective connection with the first and second adapter assemblies. The manual retraction tool includes an actuation assembly and a shaft supported by the actuation assembly. Actuation of the actuation assembly is configured to rotate the shaft about a longitudinal axis such that the shaft selectively engages the first and second end effectors via the first and second adapter assemblies.

In aspects of the present disclosure, the first and second adapter assemblies are configured for selective connection with an extension assembly. In such aspects, the extension assembly is selectively interconnected between the first and second adapter assemblies and the first and second end effectors, respectively.

In another aspect of the present disclosure, the handle housing includes a connecting portion, the first adapter assembly includes a first drive coupling assembly, and the second adapter includes a second drive coupling assembly. In such aspects, the connecting portion of the handle housing is configured to selectively receive the first and second drive coupling assemblies of the first and second adapter assemblies, respectively.

In yet another aspect of the present disclosure, the first drive coupling assembly includes a first plurality of rotatable connector sleeves, each of the first plurality of rotatable connector sleeves being arranged in a longitudinally extending common plane with one another. In such aspects, the second drive coupling assembly includes a second plurality of rotatable connector sleeves, each of the first plurality of rotatable connector sleeves being arranged in a longitudinally extending common plane with one another. In such aspects, the shaft of the manual retraction tool is configured to be selectively insertable into at least one rotatable connector sleeve of each of the first and second plurality of rotatable connector sleeves of the first and second adapter assemblies, respectively, to engage the first and second end effectors, respectively.

In still another aspect of the present disclosure, the connecting portion of the handle housing includes a plurality of drive connectors, each of the plurality of drive connectors being arranged in a longitudinally extending common plane with one another. In such aspects, the plurality of drive connectors is configured to be selectively coupled with the first plurality of rotatable connector sleeves of the first adapter assembly and the second plurality of rotatable connector sleeves of the second adapter assembly. In such aspects, each of the plurality of drive connectors is configured to independently transmit a rotational force to a corresponding rotatable connector sleeve of each of the first and second plurality of rotatable connector sleeves of the first and second adapter assemblies, respectively.

In embodiments of the present disclosure, the shaft of the manual retraction tool includes a distal end portion and a proximal end portion. In such embodiments, each of the distal end portion and the proximal end portion are dimensioned to be selectively inserted into the at least one rotatable connector sleeve of each of the first and second plurality of rotatable connector sleeves of the first and second adapter assemblies, respectively, to engage the first and second end effectors, respectively.

In one embodiment of the present disclosure, when the distal end portion of the shaft of the manual retraction tool selectively engages the first and second adapter assemblies, the manual retraction tool is configured to perform a first function. In such embodiments, when the proximal end portion of the shaft of the manual retraction tool selectively engages the first and second adapter assemblies, the manual retraction tool is configured to perform a second function, different from the first function.

In another aspect of the present disclosure, the actuation assembly of the manual retraction tool includes a trigger operably connected to the ratchet assembly. In such aspects, when the trigger is actuated from a first position towards a second position, the ratchet assembly rotates the shaft about the longitudinal axis in a first direction to selectively effect rotation of a rotatable connector of each of the first and second adapter assemblies.

BRIEF DESCRIPTION OF THE DRAWINGS

Embodiments of the present disclosure are described herein with reference to the accompanying drawings, wherein:

FIG. 11C is a side view of a crank of the manual retraction tool of FIG. 11A;

FIG. 11D is a perspective view of the manual retraction tool of FIG. 11A and shown in a second position;

FIG. 11E is a perspective view of the manual retraction tool of FIG. 11A shown in a first position with a portion of the housing removed;

FIG. 12A is a perspective view of an electromechanical surgical device in accordance with another embodiment of the present disclosure including an adapter assembly interconnected between an electromechanical surgical device and an end effector;

FIG. 12B is a perspective view illustrating a proximal end of the adapter assembly of FIG. 12A;

FIG. 12C is a representation of a manual retraction tool in accordance with an embodiment of the present disclosure.

DETAILED DESCRIPTION

Figure 1:
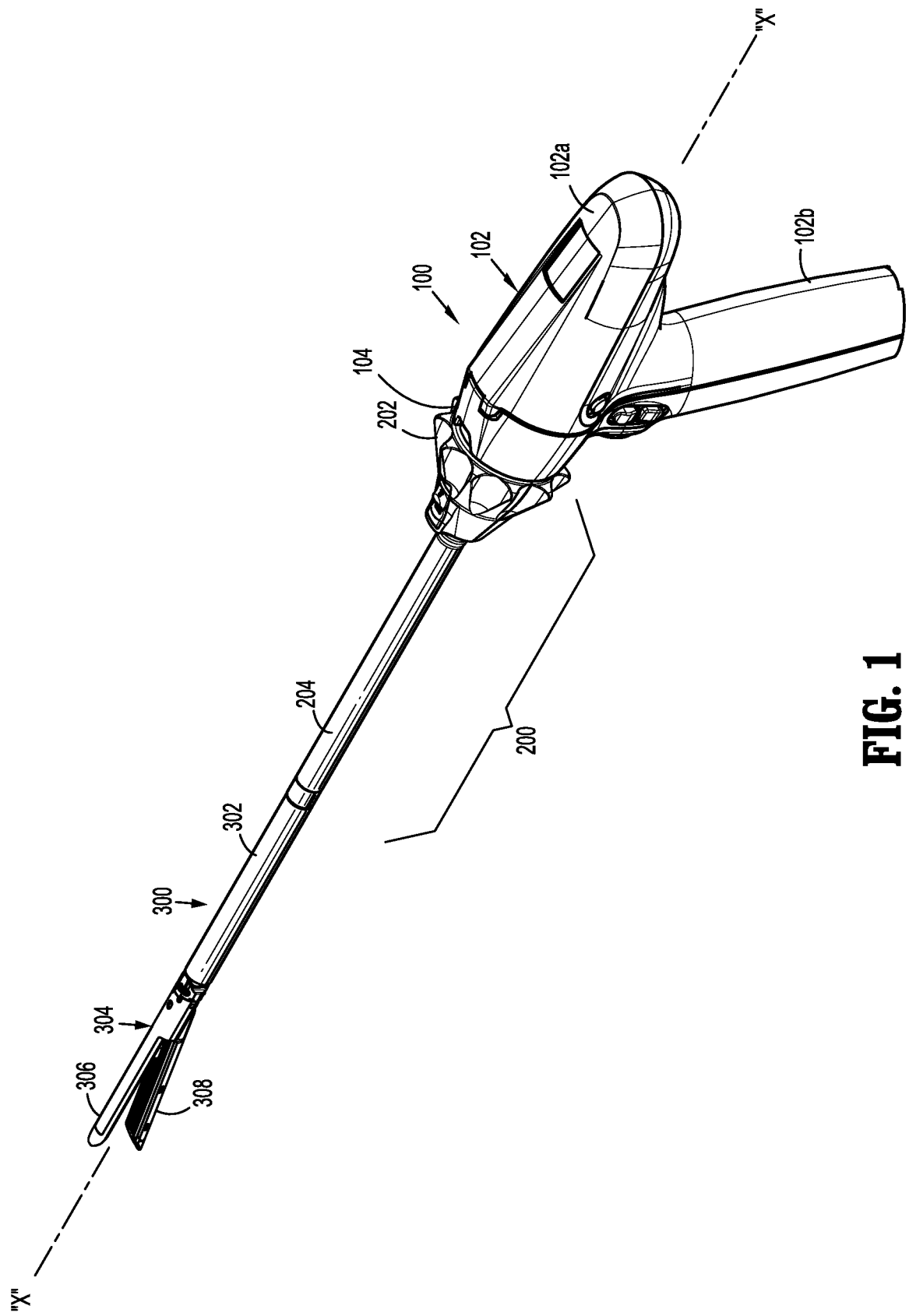
FIG. 1 is a perspective view of an electromechanical surgical device in accordance with an embodiment of the present disclosure including an adapter assembly interconnected between an electromechanical surgical device and an end effector.

Embodiments of the presently disclosed manual retraction tools for use with electromechanical surgical devices are described in detail with reference to the drawings, in which like reference numerals designate identical or corresponding elements in each of the several views. As used herein, the term "distal" refers to a portion of a structure that is farther from a clinician, while the term "proximal" refers to a portion of a structure that is closer to a clinician. As used herein, the term "clinician" refers to a doctor, nurse, or other care provider and may include support personnel.

The exemplary embodiments of a manual retraction tool, kits, and methods of use, are disclosed and discussed in terms of a tool for actuating an adapter assembly of an electromechanical surgical device to effect operation of an end effector. However, it should be appreciated that the present disclosure may be used in a range of electrosurgical devices.

As illustrated in FIG. 1, an exemplary electromechanical surgical device 100 includes an adapter assembly 200 configured for selective connection with an end effector 300 (e.g., multiple- or single-use loading units, etc.). A manual retraction tool of the present disclosure is configured to operatively couple with the adapter assembly 200 of the electromechanical surgical device 100 to actuate the adapter assembly 200 to effect operation of the end effector 300.

A plurality of different end effectors may be connected to adapter assembly 200, each end effector being configuration for actuation and manipulation by the powered handheld electromechanical surgical device 100. For the purposes of discussion, the end effectors will be discussed in terms of surgical loading units; however, electromechanical surgical device 100 can be used with a variety of end effectors 300 within the purview of those skilled in the art, such as, for example, clamping jaws and cutting tools.

The electromechanical surgical device 100 includes a handle housing 102 including a circuit board (not shown) and a drive mechanism (not shown) situated therein. The circuit board is configured to control the various operations of electromechanical surgical device 100. Handle housing 102 defines a cavity therein (not shown) for selective removable receipt of a battery (not shown). The battery is configured to supply power to any of the electrical components of electromechanical surgical device 100.

Handle housing 102 includes an upper housing portion 102a which houses various components of electromechanical surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of electromechanical surgical device 100 that is connected to or supporting adapter assembly 200 and/or loading unit 300.

Handle housing 102 provides a housing in which the drive mechanism is situated and supports a plurality of finger-actuated control buttons, rocker devices, and the like for activating various functions of electromechanical surgical device 100. The drive mechanism is configured to drive shafts and/or gear components in order to perform the various operations of electromechanical surgical device 100. In particular, the drive mechanism is configured to drive shafts and/or gear components in order to selectively move a tool assembly 304 of loading unit 300 relative to a proximal body portion 302 of loading unit 300, to rotate loading unit 300 about a longitudinal axis "A-A" relative to handle housing 102, and to move/approximate an anvil assembly 306 and a cartridge assembly 308 of loading unit 300 relative to one another, and/or to fire a stapling and cutting cartridge within cartridge assembly 308 of loading unit 300.

Figure 2:
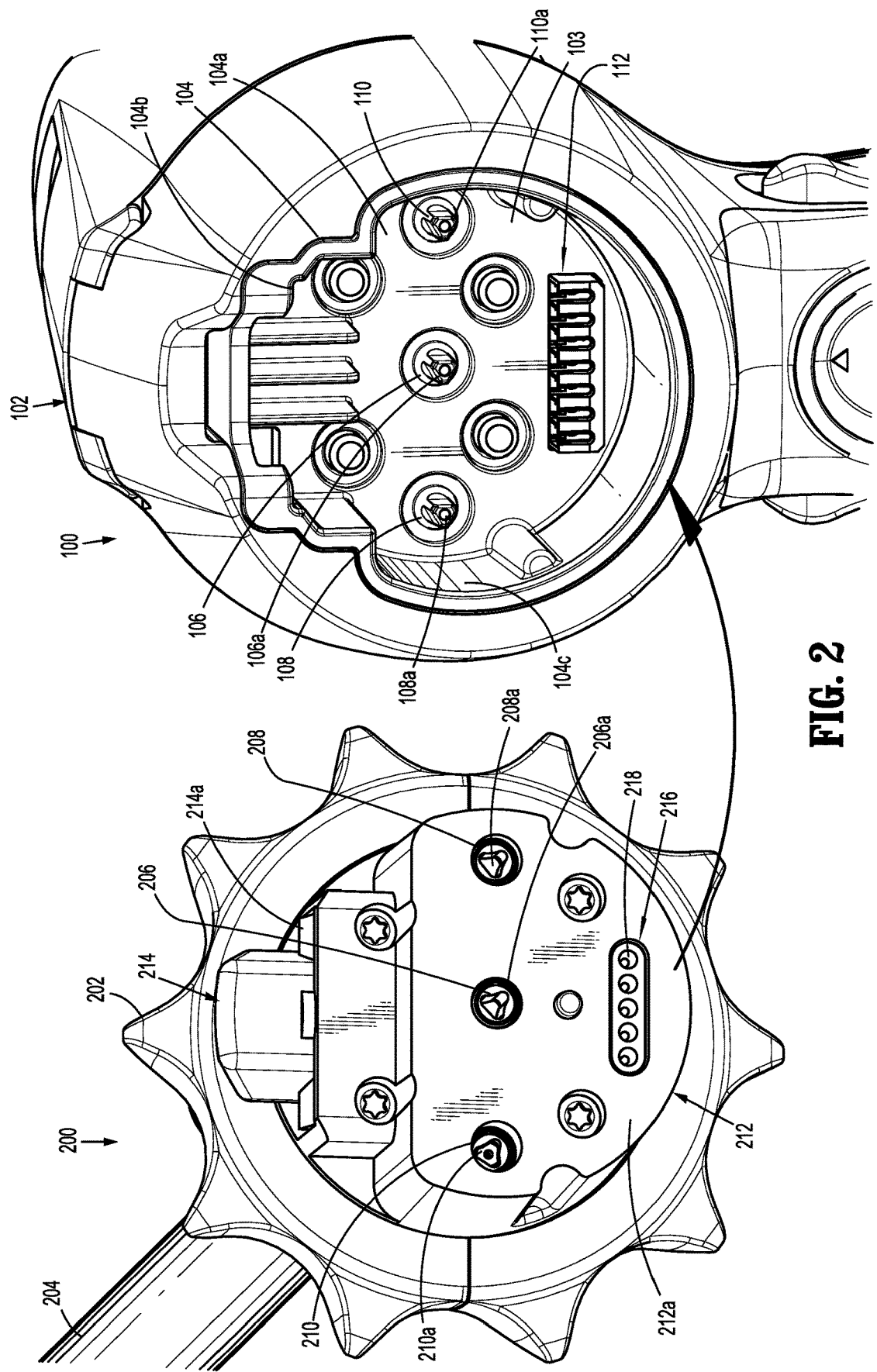
FIG. 2 is a perspective view illustrating an attachment of a proximal end of the adapter assembly to a distal end of the electromechanical surgical device of FIG. 1.

As shown in FIG. 2, in conjunction with FIG. 1, handle housing 102 defines a connecting portion 104 configured to accept a corresponding drive coupling assembly 212 of adapter assembly 200. Specifically, connecting portion 104 of electromechanical surgical device 100 has a distal facing recess 104a that receives a proximal facing cap 212a of drive coupling assembly 212 of adapter assembly 200 when adapter assembly 200 is mated to handle housing 102. Connecting portion 104 houses three rotatable drive connectors 106, 108, 110 which are arranged in a common plane or line with one another.

When adapter assembly 200 is mated to handle housing 102, each of rotatable drive connectors 106, 108, 110 of handle housing 102 couples with a corresponding rotatable connector sleeve 206, 208, 210 of adapter assembly 200. In this regard, the interface between corresponding first drive connector 106 and first connector sleeve 206, the interface between corresponding second drive connector 108 and second connector sleeve 208, and the interface between corresponding third drive connector 110 and third connector sleeve 210 are keyed such that rotation of each of drive connectors 106, 108, 110 of handle housing 102 causes a corresponding rotation of corresponding connector sleeve 206, 208, 210 of adapter assembly 200. Each of drive connectors 106, 108, 110 includes a tri-lobe tip 106a, 108a, 110a extending distally beyond a wall 103 of connecting portion 104, and each of connector sleeve 206, 208, 210 includes a tri-lobe recess 206a, 208a, 210a for receiving corresponding tip-lobe tip 106a, 108a, 110a. However, it should be understood that the shape of the tips and the recesses may be any shape that enables the drive connectors to rotate the connector sleeves.

The mating of drive connectors 106, 108, 110 of handle housing 102 with connector sleeves 206, 208, 210 of adapter assembly 200 allows rotational forces to be independently transmitted via each of the three respective connector interfaces. Drive connectors 106, 108, 110 of handle housing 102 are configured to be independently rotated by the drive mechanism of electromechanical surgical device 100. In this regard, a function selection module (not shown) of the drive mechanism selects which drive connector or connectors 106, 108, 110 of handle housing 102 is to be driven by the motor of electromechanical surgical device 100.

Since each of drive connectors 106, 108, 110 of handle housing 102 has a keyed and/or substantially non-rotatable interface with respective connector sleeves 206, 208, 210 of adapter assembly 200, when adapter assembly 200 is coupled to handle housing 102, rotational force(s) are selectively transferred from the drive mechanism of handle housing 102 to adapter assembly 200.

The selective rotation of drive connector(s) 106, 108, 110 of handle housing 102 allows electromechanical surgical device 100 to selectively actuate different functions of loading unit 300. For example, selective and independent rotation of first drive connector 106 of handle housing 102 corresponds to the selective and independent opening and closing of tool assembly 304 of loading unit 300, and driving of a stapling/cutting component of tool assembly 304 of loading unit 300. As an additional example, the selective and independent rotation of second drive connector 108 of handle housing 102 corresponds to the selective and independent articulation of tool assembly 304 of loading unit 300 transverse to longitudinal axis "A-A." Additionally, for instance, the selective and independent rotation of third drive connector 110 of handle housing 102 corresponds to the selective and independent rotation of loading unit 300 about longitudinal axis "A-A" relative to handle housing 102 of electromechanical surgical device 100.

Adapter assembly 200 includes an outer knob housing 202 and an outer tube 204 extending from a distal end of knob housing 202. Knob housing 202 and outer tube 204 are configured and dimensioned to house the components of adapter assembly 200. Outer tube 204 is dimensioned for endoscopic insertion, in particular, outer tube 204 is passable through a typical trocar port, cannula, or the like. Knob housing 202 is dimensioned to not enter the trocar port, cannula, or the like. Knob housing 202 is configured and adapted to connect to connecting portion 104 of handle housing 102 of electromechanical surgical device 100.

Adapter assembly 200 includes a plurality of force/rotation transmitting/converting assemblies disposed therein. Each force/rotation transmitting/converting assembly is configured and adapted to transmit/convert a speed/force of rotation (e.g., increase or decrease) of first, second and third drive connectors 106, 108, 110 of handle housing 102 before transmission of such rotational speed/force to loading unit 300.

Adapter assembly 200 further includes an attachment/detachment button 214 supported thereon. Specifically, button 214 is supported on drive coupling assembly 212 of adapter assembly 200 and is biased to an un-actuated condition. Button 214 includes at least one lip or ledge 214a formed therewith that is configured to snap behind a corresponding lip or ledge 104b defined along recess 104a of connecting portion 104 of handle housing 102. In use, when adapter assembly 200 is connected to handle housing 102, lip 214a of button 214 is disposed behind lip 104b of connecting portion 104 of handle housing 102 to secure and retain adapter assembly 200 and handle housing 102 with one another. In order to permit disconnection of adapter assembly 200 and handle housing 102 from one another, button 214 is depresses or actuated, against its bias condition, to disengage lip 214a of button 214 and lip 104b of connecting portion 104 of handle housing 102.

Adapter assembly 200 includes an electrical assembly 216 supported on and in outer knob housing 202. Electrical assembly 216 includes a plurality of electrical contact pins 218, supported on a circuit board (not shown), for electrical connection to a corresponding electrical plug 112 disposed in connecting portion 104 of handle housing 102. Electrical assembly 216 serves to allow for calibration and communication of life-cycle information to the circuit board of electromechanical surgical device 100 via electrical plug 112 that are electrically connected to the circuit board (not shown) of electromechanical surgical device 100.

For a detailed description of the construction and operation of exemplary electromechanical surgical devices 100, adapter assemblies 200, and loading units 300, reference may be made to International Application No. PCT/US2008/077249, filed Sep. 22, 2008 (Inter. Pub. No. WO 2009/039506), U.S. Pat. No. 7,819,896, filed on Aug. 31, 2009, U.S. Patent Publication No. 10,588,629, filed on Nov. 20, 2009, and U.S. Patent Publication No. 9,597,104, filed on May 2, 2013, the entire contents of each of which are incorporated herein by reference.

In accordance with the present disclosure, adapter assembly 200 and loading unit 300 when connected to one another, may constitute a surgical implement or surgical tool assembly. Turning now to FIGS. 3-11, electromechanical surgical device 100 includes a manual retraction tool, as detailed below, to actuate the adapter assembly 200 in order to manually articulate and/or fire/retract electromechanical surgical device 100 in the event that electromechanical surgical device 100 fails to work, such as, for example, in the event that the batteries fail, there is a programing error, or there is a software error, etc.

Figure 3:
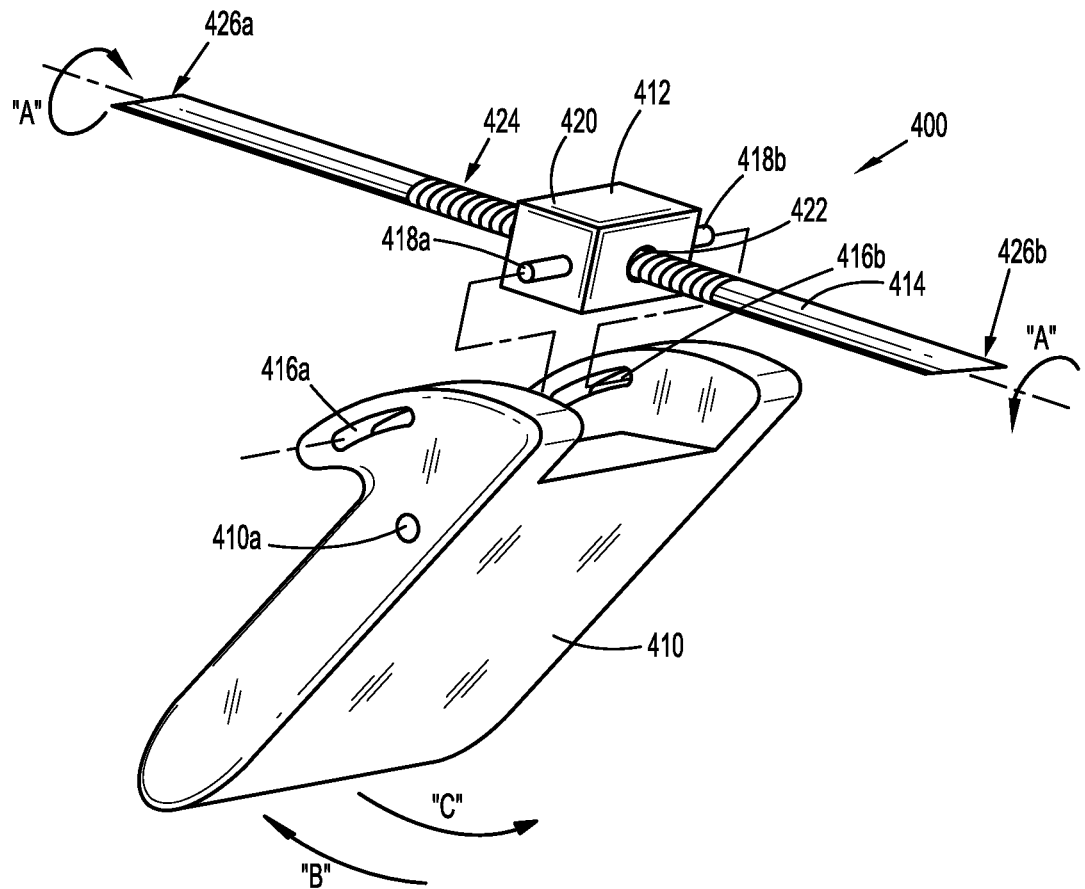
FIG. 3 is a perspective view of a manual retraction tool in accordance with an embodiment of the present disclosure.

With reference to FIG. 3, an embodiment of a manual retraction tool 400 for use with an electromechanical surgical device, such as the one described above, and more specifically with adapter assembly 200, is shown. Manual retraction tool 400 includes a trigger 410 (connected to a fixed handle (not shown)) which is configured to engage a rotation mechanism, for example, a nut 412, which in turn rotates a shaft 414 to either retract or fire loading unit 300 loaded onto adapter assembly 200 of electromechanical surgical device 100.

Trigger 410 is spring loaded or biased to a starting position given by arrow "B." However, upon actuation, trigger 410 is rotatable about a pivot 410a in a direction given by arrow "C" to engage nut 412. Trigger 410 includes a pair of opposing slots 416a and 416b which are configured to locate opposing posts 418a and 418b extending from nut 412. Nut 412 includes an outer surface 420 defining a through-hole 422 therethrough. Through-hole 422 is configured for rotatably supporting shaft 414 as shaft 414 rotates about a longitudinal axis "A-A" relative to nut 412. As shown in FIG. 3, shaft 414 includes a threaded portion 424 configured to engage an inner threaded portion (not shown) of through-hole 422 of nut 412. Though shaft 414 is shown to include a threaded portion 424, it is contemplated that the entirety of shaft 414 may be threaded. Shaft 414 also includes a distal tip 426a and a proximal tip 426b. In embodiments, distal tip 426a and proximal tip 426b include a trilobe configuration. However, it is contemplated that distal tip 426a and proximal tip 426b may include any suitable configuration.

Figure 4:
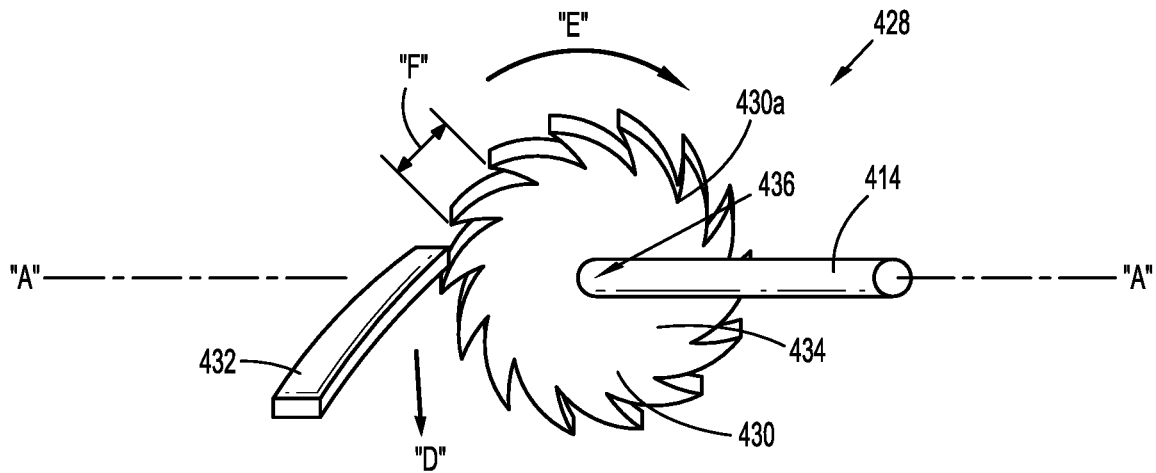
FIG. 4 is a perspective view of an alternative embodiment of the manual retraction tool of FIG. 3.

In embodiments, manual retraction tool 400 includes a ratchet assembly 428. As shown in FIG. 4, ratchet assembly 428 includes a ratchet wheel 430 and a biasing member, such as, for example, a leaf spring 432 biased in a direction given by arrow "D." Ratchet wheel 430 includes a plurality of teeth 430a with a distance "F" between each tooth. Ratchet wheel 430 is configured to freely rotate about longitudinal axis "A-A" in a first direction given by arrow "E." However, if ratchet wheel 430 attempts to rotate in a second direction, opposite to the first direction given by arrow "E," the rotation of ratchet wheel 430 is limited by the distance "F" between each tooth 430a. It is contemplated that this function of ratchet assembly 428 may be used to prevent shaft 414 from translating in the second opposite direction about longitudinal axis "A-A" when the trigger 410 returns to the starting position given by arrow B. To that end, ratchet wheel 430 includes an outer surface 434 defining a through-hole 436 configured for supporting shaft 414 therethrough. It is contemplated that ratchet wheel 430 is secured to shaft 414 in any suitable manner such as, for example, adhesives and/or welding, so that ratchet wheel 430 and shaft 414 are not independently rotatable relative to one another.

In use, when trigger 410 is actuated in the direction given by arrow "C," nut 412 is driven along threaded portion 424 of shaft 414. As a result, shaft 414 is rotated about longitudinal axis "A-A" with respect to nut 412 in the first direction given by arrow "E." It is contemplated that manual retraction tool 400 performs different functions depending on whether distal tip 426a or proximal tip 426b is inserted into rotatable connector sleeve 206, 208, 210 of adapter assembly 200. For example, in embodiments, when distal tip 426a is inserted into rotatable connector sleeve 206, 208, 210 of adapter assembly 200, actuation of tool 400 causes retraction of loading unit 300 and when proximal tip 426b is inserted in rotatable connector sleeve 206, 208, 210 of adapter assembly 200, actuation of manual retraction tool 400 causes loading unit 300 to fire or clamp.

In embodiments where manual retraction tool 400 includes the ratchet assembly 428, when shaft 414 is rotated about longitudinal axis "A-A" with respect to nut 412 in the first direction given by arrow "E," upon an opening of trigger 410, leaf spring 432 engages the plurality of teeth 430a of ratchet wheel 430 and prevents ratchet wheel 430 from rotating about longitudinal axis "A-A" with respect to nut 412 in the second opposite direction given by arrow "D." As a result, shaft 414 is prevented from rotating about longitudinal axis "A-A" with respect to nut 412 in the direction given by arrow "D."

Figure 5A:
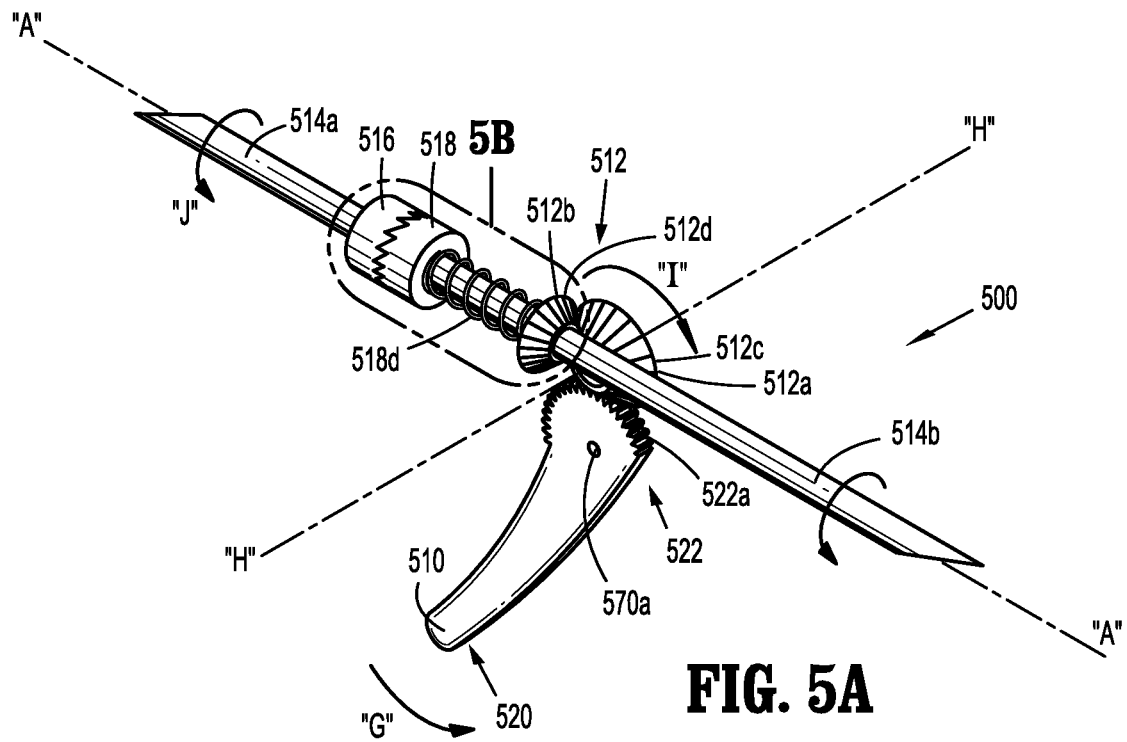
FIG. 5A is a perspective view of a manual retraction tool in accordance with another embodiment of the present disclosure.
Figure 5B:
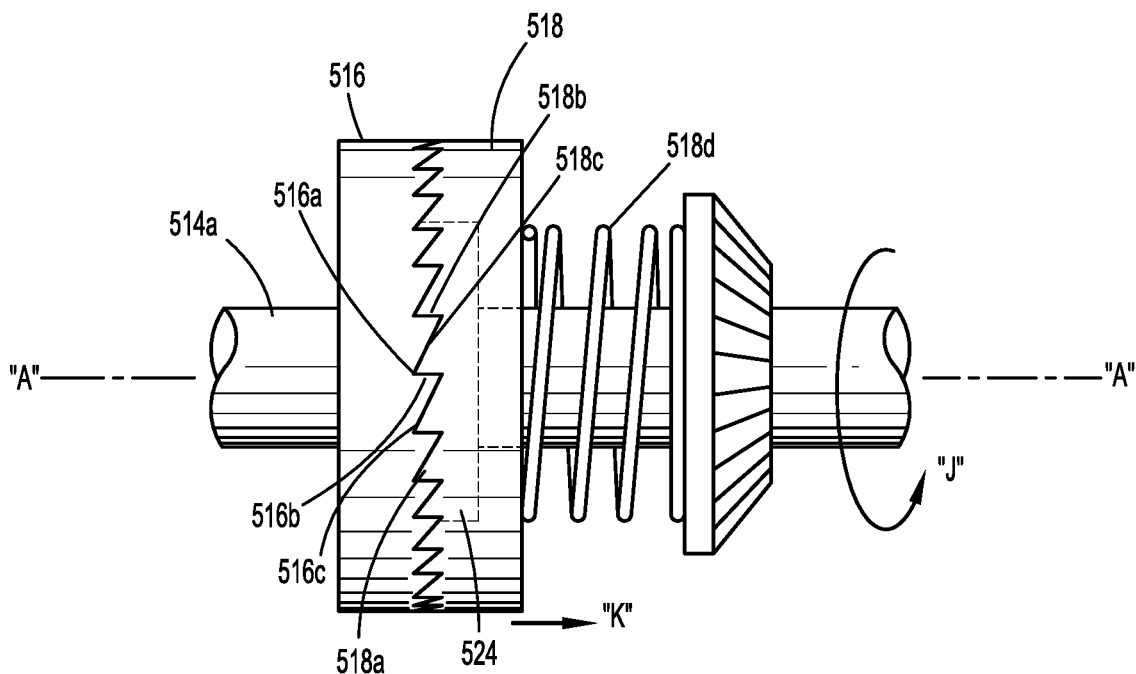
FIG. 5B is an enlarged view of the indicated area of detail of FIG. 5A.

Turning now to FIGS. 5A and 5B, an embodiment of a manual retraction tool 500 for use with an electromechanical surgical device, such as the one described above is shown. Manual retraction tool 500 is similar to manual retraction tool 400 disclosed above and will therefore be described to the extent necessary to highlight its differences.

Manual retraction tool 500 includes a trigger 510 (connected to a fixed handle (not shown)), a gear assembly 512, a distal shaft 514a, a proximal shaft 514b, a ratchet wheel 516 fixed to distal shaft 514a, and a clutch 518 slidably located on proximal shaft 514b and configured to operatively engage ratchet wheel 516. Trigger 510 extends between a proximal or first portion 520 and a distal or second portion 522. Distal portion 522 includes a plurality of teeth 522a configured to engage gear assembly 512. In particular, gear assembly 512 includes a first gear 512a and a second gear 512b. In embodiments, first and second gears 512a and 512b are bevel gears. However, in alternative embodiments, it is contemplated that any suitable type of gear may be used. First gear 512a includes a plurality of teeth 512c and second gear 512b includes a plurality of teeth 512d. As shown in FIG. 5A, the plurality of teeth 512c of first gear 512a are operatively engaged with the plurality of teeth 522a of trigger 510 as well as the plurality of teeth 512d of second gear 512b. Accordingly, when trigger 510 is rotated about a pivot 510a in a direction given by arrow "G," first gear 512a is configured to rotate about axis "H-H" relative to second gear 512b in a direction given by arrow "I." The rotation of first gear 512a in turn rotates second gear 512b about longitudinal axis "A-A" relative to first gear 512a in a first direction given by arrow "J."

Turning now to FIG. 5B in conjunction with FIG. 5A, as noted above, manual retraction tool 500 includes a clutch 518 configured to operatively engage ratchet wheel 516 to rotate distal shaft 514a about longitudinal axis "A-A" relative to trigger 510. To that end, clutch 518 includes a plurality of mating features, such as, for example, a plurality of teeth 518a configured to engage a plurality of teeth 516a defined in ratchet wheel 516. As shown in FIG. 5B, the plurality of teeth 518a of clutch 518 includes a flat portion 518b and an angled portion 518c. Similarly, the plurality of teeth 516a of ratchet wheel 516 includes a correspondingly shaped flat portion 516b and a correspondingly shaped angled portion 516c. As such, when clutch 518 engages ratchet wheel 516, the plurality of teeth 518a of clutch 518 sit flush with the plurality of teeth 516a of ratchet wheel 516. It is contemplated that this configuration of the plurality of teeth 518a of clutch 518 and the plurality of teeth 516a of ratchet wheel 516 enables distal shaft 514a to rotate only in one direction. In particular, it is contemplated that ratchet wheel 516 is only rotatable when clutch 518 rotates in the first direction about longitudinal axis "A-A" with respect to trigger 510 in the direction given by arrow "J." During this rotation, flat portion 518b of the plurality of teeth 518a of clutch 518 engages flat portion 516b of the plurality of teeth 516a of ratchet wheel 516 to rotatably drive ratchet wheel 516 counter-clockwise about longitudinal axis "A-A" with respect to trigger 510 in the direction given by arrow "J." However, if clutch 518 attempts to rotate in a second opposite direction about longitudinal axis "A-A" with respect to trigger 510, angled portion 518c of the plurality of teeth 518a of clutch 518 engage the angled portion 516c of the plurality of teeth 516a of ratchet wheel 516. The angular engagement between angled portion 518c of the plurality of teeth 518a of clutch 518 and angled portion 516c of the plurality of teeth 516a of ratchet wheel 516 causes clutch 518 to slip in a direction given by arrow "K" against the resilient bias of a spring 518d, the details of which will be discussed below.

In embodiments, clutch 518 is spring loaded and includes a biasing member, such as, for example, spring 518d. Though spring 518d, in FIGS. 5A and 5B, is shown as a coil spring, it is contemplated that any suitable biasing member may be used. Spring 518d is resiliently biased distally and is configured to urge clutch 518 to engage ratchet wheel 516. In order to retain clutch 518 on proximal shaft 514b, it is contemplated that a clamp 524 may be used. In embodiments, clamp 524 is located on proximal shaft 514b between ratchet wheel 516 and clutch 518 to prevent distal translation of clutch 518 beyond clamp 524.

In use, when trigger 510 of manual retractor 500 is actuated, first gear 512a rotates about axis "H-H" relative to second gear 512b in the direction given by "I." The rotation of first gear 512a in turn rotates second gear 512b and proximal shaft 514b in the first direction about longitudinal axis "A-A" relative to first gear 512a given by the arrow "J." As described above, spring 518d is resiliently biased distally and therefore urges clutch 518 to engage ratchet wheel 516. Due to the rotation of second gear 512b and proximal shaft 514b, clutch 518 also rotates about longitudinal axis "A-A" relative to first gear 512a in the first direction given by the arrow "J." As a result, flat portion 518b of the plurality of teeth 518a of clutch 518 engage flat portion 516b of the plurality of teeth 516a of ratchet wheel 516 to rotatably drive ratchet wheel 516 about longitudinal axis "A-A" with respect to trigger 510 in the direction given by arrow "J." The rotation of ratchet wheel 516 rotates distal shaft 514a to actuate adapter assembly 200 of electromechanical surgical device 100 to manually fire or retract electromechanical surgical device 100.

When trigger 510 is released, clutch 518 rotates about longitudinal axis "A-A" in the second opposite direction and angled portion 518c of the plurality of teeth 518a of clutch 518 engage the angled portion 516c of the plurality of teeth 516a of ratchet wheel 516. As described above, the angular engagement between angled portion 518c of the plurality of teeth 518a of clutch 518 and angled portion 516c of the plurality of teeth 516a of ratchet wheel 516 causes clutch 518 to slip in a direction given by arrow "K" against the resilient bias of spring 518b. The slipping of clutch 518 prevents ratchet wheel 516 from also rotating in the second direction about the longitudinal axis "A-A" and undoing the work of actuating trigger 510.

Figure 6A:
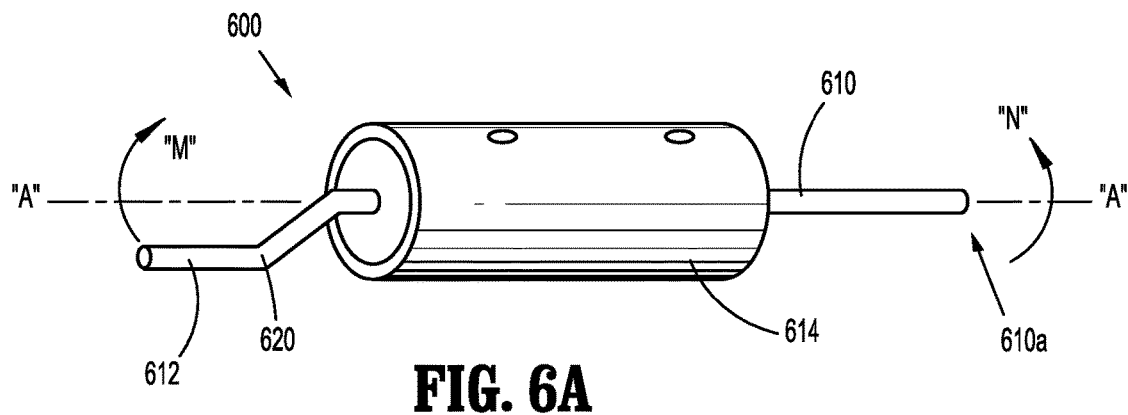
FIG. 6A is a perspective view of a manual retraction tool in accordance with another embodiment of the present disclosure.
Figure 6B:
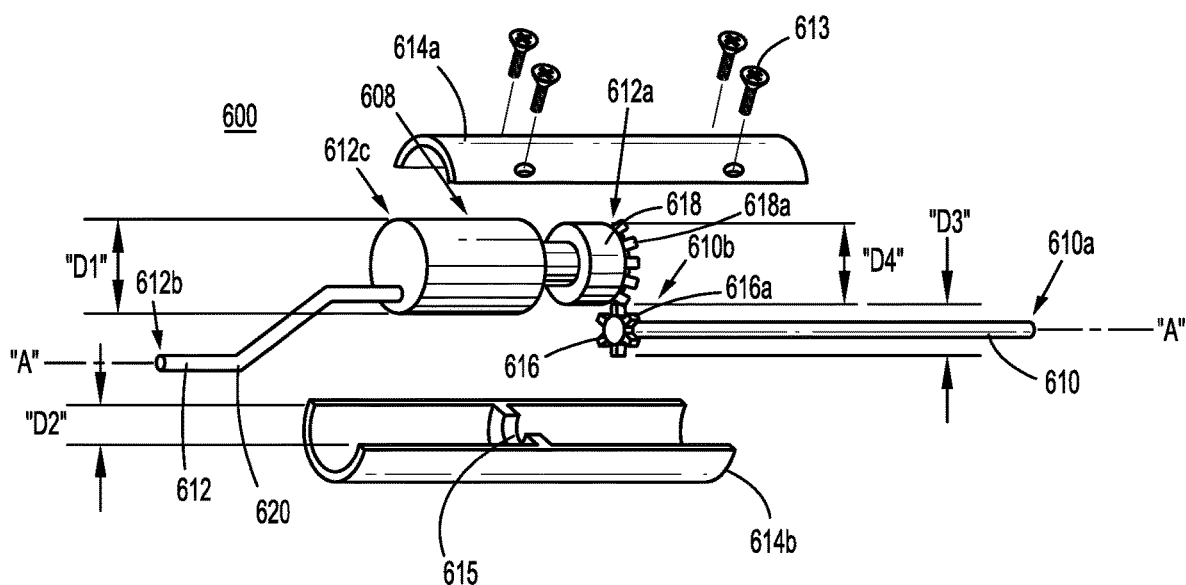
FIG. 6B is an exploded view of the manual retraction tool according to FIG. 6A.

Turning now to FIGS. 6A and 6B, an embodiment of a manual retraction tool 600 for use with an electromechanical surgical device, such as the one described above is shown.

Manual retraction tool 600 includes a shaft assembly 608 having a distal shaft 610 and a proximal shaft 612, and a housing 614 enclosing at least a portion of shaft assembly 608.

As shown in FIG. 6B, distal shaft 610 extends between a distal portion 610*a* and a proximal portion 610*b*. Similarly, proximal shaft 612 extends between a distal portion 612*a* and a proximal portion 612*b*. Proximal shaft 612 also includes a body portion 612*c* between distal portion 612*a* and proximal portion 612*b*.

Housing 614 includes top or first half portion 614*a* and a bottom or second half portion 614*b*. In embodiments, top portion 614*a* and bottom portion 614*b* together form a cylindrical housing 614 as shown in FIG. 6A. However, other housing shapes, such as, for example, a rectangular housing, is contemplated. Bottom portion 614*b* of housing 614 includes a support structure, such as, for example, a ledge 615 configured to support body portion 612*c*. Though it is not shown, it is contemplated that top portion 614*a* of housing 614 includes a similar support structure configured to support body portion 612*c*. In embodiments, a plurality of fasteners 613 are used to secure top portion 614*a* to bottom portion 614*b*. However, it is contemplated that other methods of securing top portion 614*a* to bottom portion 614*b*, such as, for example, adhesives or welding, may be used.

Body portion 612*c* of proximal shaft 612 includes a cross-sectional diameter "D1" and housing 614 includes an inner diameter of "D2." It is contemplated that diameter "D1" and "D2" are correspondingly sized such that the movement of body portion 612*c* of proximal shaft 612 is restricted when inside housing 614. Said another way, when body portion 612*c* of proximal shaft 612 is located inside housing 614, it is contemplated that there is minimal clearance between body portion 612*c* and housing 614.

Proximal portion 610*b* of distal shaft 610 includes a gear 616 and distal portion 612*a* of proximal shaft 612 includes a gear 618. In embodiments, gears 616 and 618 are spur gears. However, it is contemplated that any suitable gears may be used. Gear 618 of proximal shaft 612 includes a plurality of teeth 618*a* configured to engages a plurality of teeth 616*a* of gear 616 of distal shaft 610. In embodiments, gear 616 includes a diameter "D3" and gear 618 includes a diameter "D4," where diameter "D3" of gear 616 is smaller than diameter "D4" of gear 618. It is contemplated that using a larger gear 618 to drive a smaller gear 616 achieves greater than a 1:1 rotation ratio.

Proximal portion 612*b* of proximal shaft 612 includes a crank 620 configured for rotating proximal shaft 612 and in turn distal shaft 610. Crank 620 includes a bent configuration. It is contemplated that the bent configuration of crank 620 will give a user greater mechanical advantage in rotating the manual retractor 600. Further, it is contemplated that crank 620 of manual retractor 600 can be rotated both clockwise and counter-clockwise about longitudinal axis "A-A" relative to housing 614. Depending on the direction of rotation, manual retractor 600 can actuate adapter assembly 200 of electromechanical surgical device 100 to either fire or retract electromechanical surgical device 100.

In use, when crank 620 is rotated about longitudinal axis "A-A" with respect to housing 614 in a first direction given by arrow "M," distal shaft 610 is rotated in a opposite second direction about longitudinal axis "A-A" in a direction given by arrow "N." In particular, the rotation of crank 620 in the direction of arrow "M," rotates gear 618 of proximal shaft in the direction of arrow "M." As a result of the engagement between the plurality of teeth 618*a* of gear 618 and the plurality of teeth 616*a* of gear 616, the rotation of gear 618 in the direction of arrow "M," rotates gear 616 of distal shaft 610 in the opposite direction given by arrow "N." Similarly, when crank 620 is rotated in the direction of arrow "N" about longitudinal axis "A-A," distal shaft 610 is rotated in the direction of arrow "M" about longitudinal axis "A-A." As noted above, depending on the direction of rotation, manual retractor 600 is able to actuate adapter assembly 200 of electromechanical surgical device 100 to both fire and retract electromechanical surgical device 100.

Figure 7A:
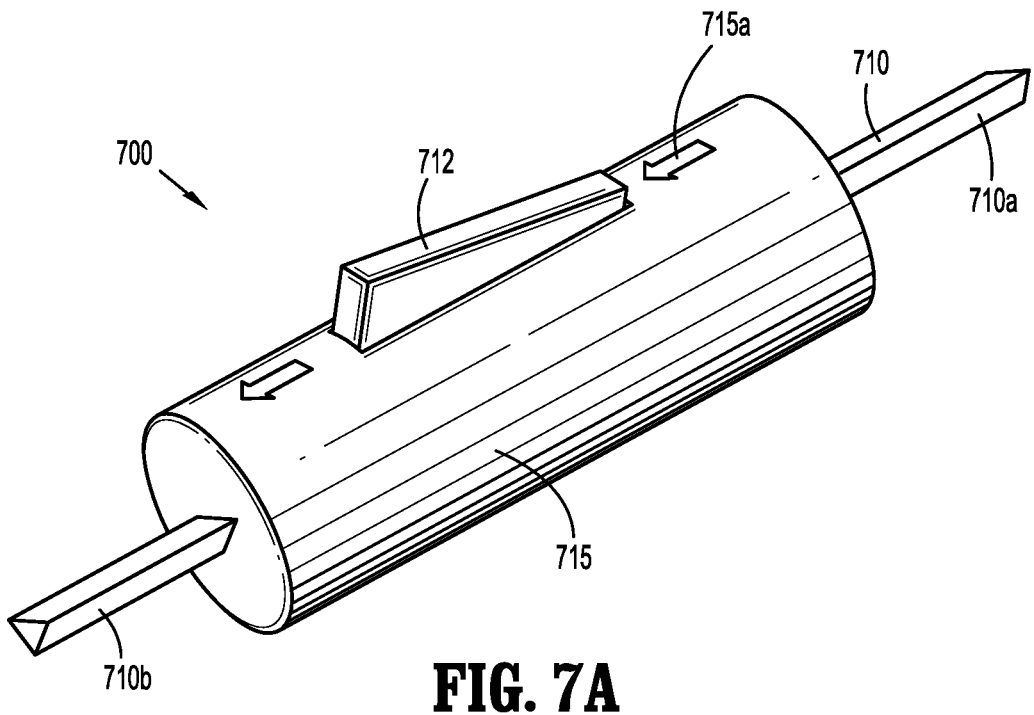
FIG. 7A is a perspective view of a manual retraction tool in accordance with another embodiment of the present disclosure.
Figure 7B:
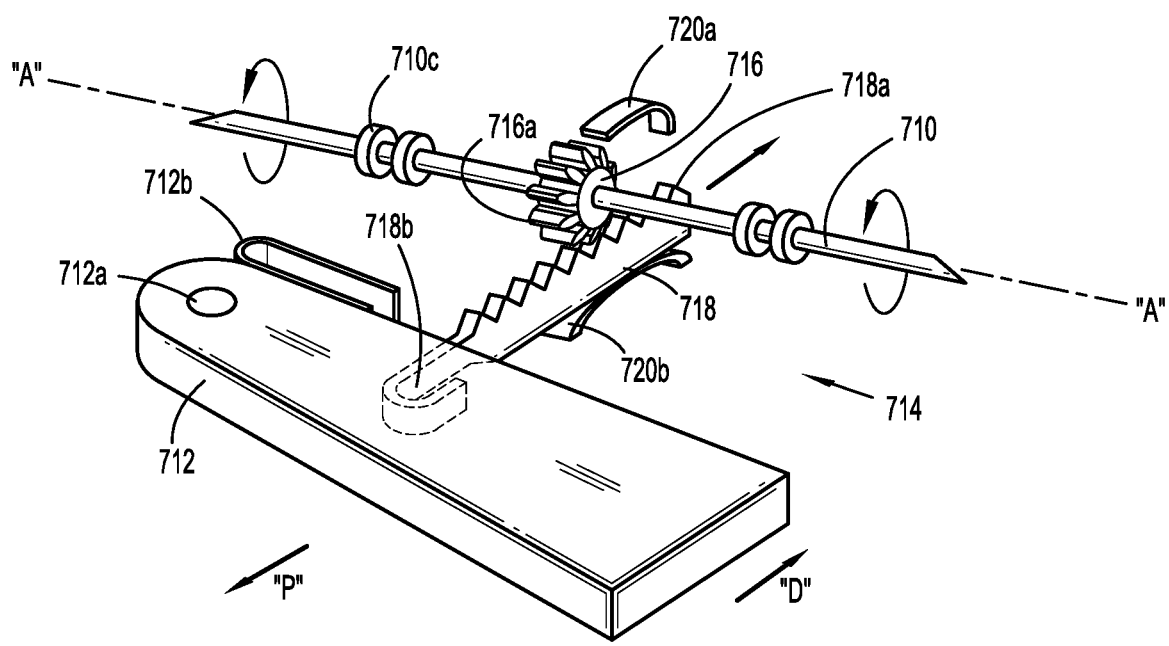
FIG. 7B is a perspective view of the manual retraction tool according to FIG. 7A with the housing removed.

Turning now to FIGS. 7A and 7B, an embodiment of a manual retraction tool 700 for use with an electromechanical surgical device, such as the one described above is shown. Manual retraction tool 700 includes a shaft 710, a trigger 712, a ratchet assembly 714, and a housing 715 enclosing at least a portion of shaft 710 and ratchet assembly 714.

Shaft 710 of manual retraction tool 700 extends between a distal end 710*a* and a proximal end 710*b*. Distal end 710*a* and proximal end 710*b* of shaft 710 each include a tri-lobe shape corresponding to the shape of tri-lobe tips 106*a*, 108*a*, 110*a* of drive connectors 106, 108, 110 of electromechanical surgical device 100 (see FIG. 2). However, it is contemplated that the shape of distal end 710*a* and proximal end 710*b* of shaft 710 may be any shape corresponding to the shape of a drive connector of a surgical device.

It is contemplated that both the distal end 710*a* and the proximal end 710*b* of shaft 710 may be used with adapter assembly 200 of electromechanical surgical device 100. In embodiments, distal end 710*a* of shaft 710 may be used to actuate adapter assembly 200 of electromechanical surgical device 100 to manually retract electromechanical surgical device 100, and proximal end 710*b* of shaft 710 may be used to actuate adapter assembly 200 of electromechanical surgical device 100 to manually retract electromechanical surgical device 100. However, in alternative embodiments, the opposite orientation is also contemplated.

In embodiments, housing 715 may include indicia, such as, for example an arrow 715*a*, in order to inform a user of which end of shaft 710 to use for a given operation.

Shaft 710 of manual retraction tool 700 is supported by a plurality of bushings 710*c*. The plurality of bushings 710*c* are configured for aligning shaft 710 to corresponding support structures (not shown) within housing 715.

As shown in FIG. 7B, trigger 712 of manual retraction tool 700 includes a pivot 712*a* about which trigger 712 rotates relative to housing 715, from a first position to a second position, in a direction given by arrow "O," and, from the second position to the first position, in a direction given by arrow "P." Trigger 712 is acted upon by a biasing member, such as, for example, spring 712*b*. Spring 712*b* is resiliently biased in the direction given by arrow "P" to return trigger 712 to the starting position. In embodiments, spring 712*b* is a leaf spring, however, it is contemplated that spring 712*b* may be any biasing member suitable to return trigger 712 back to the starting position.

Continuing with FIG. 7B, an embodiment of ratchet assembly 714 of manual retractor 700 is shown. Ratchet assembly 714 includes a pinion, such as, for example, a ratchet wheel 716. Ratchet wheel 716 is secured to shaft 710 such that a rotation of ratchet wheel 716 rotates shaft 710 in the same direction. It is contemplated that ratchet wheel 716 is fixed to shaft 710 in any suitable manner, such as, for example, welding and/or adhesives. Ratchet wheel 716 includes a plurality of teeth 716*a*.

Ratchet assembly 714 also includes a rack 718 configured for engaging ratchet wheel 716. In particular, rack 718 includes a plurality of teeth 718*a* configured for engaging the plurality of teeth 716*a* of ratchet wheel 716. Rack 718 is pivotably supported on trigger 712 at a pivot 718*b*. It is contemplated that rack 718 is independently pivotable about pivot 718*b* with respect to trigger 712.

Ratchet assembly 714 also includes a first biasing member 720*a* and a second biasing member 720*b*. Though first and second biasing members 720*a* and 720*b* are shown to be leaf springs, it is contemplated that any suitable biasing member may be used. First biasing member 720*a* is in the form of a pawl or finger that is configured to prevent rotation of ratchet wheel 716 in a second, clockwise direction about longitudinal axis "A-A" with respect to rack 718. Second biasing member 720*b* is located adjacent rack 718 and is configured to bias rack 718 into engagement with ratchet wheel 716 such that when trigger 712 is actuated, ratchet wheel 716 is rotated about longitudinal axis "A-A" in a first, counter clockwise direction. However, during the return stroke of trigger 712 when ratchet wheel 716 is held in place by first biasing member or pawl 720*a*, rack 718 is able to disengage from ratchet wheel 716 so that trigger 712 is able to return to the starting position in the direction given by arrow "P."

In use, when trigger 712 is actuated/squeezed, trigger 712 rotates about pivot 712*a* with respect to housing 715 in the direction given by arrow "O." Upon actuation of trigger 712, rack 718 is transversely translated with respect to longitudinal axis "A-A" in a direction given by arrow "O." As noted above, the second biasing member 720*b* is biased to keep rack 718 engaged with ratchet wheel 716. More specifically, the second biasing member 720*b* is biased to keep the plurality of teeth 718*a* of rack 718 engaged with the plurality of teeth 716*a* of ratchet wheel 716. Due to the engagement between rack 718 and ratchet wheel 716, when rack 718 is transversely translated in the direction of arrow "O," ratchet wheel 716 is rotated in a first direction about longitudinal axis "A-A" with respect to rack 718. Since ratchet wheel 716 is fixed to shaft 710, the counter-clockwise rotation of ratchet wheel 716 also rotates shaft 710 counter-clockwise about longitudinal axis "A-A" with respect to rack 718. At this point, depending on which end of shaft 710 is inserted into adapter assembly 200 of electromechanical surgical device 100, electromechanical surgical device 100 is either manually retracted or manually fired.

Upon release of trigger 710, spring 712*b* urges trigger 710 back to the starting position in the direction given by arrow "P." During this return stroke of trigger 710, rack 718 is transversely translated with respect to longitudinal axis "A-A" in the direction given by arrow "P." However, pawl 720 prevents ratchet wheel 716 from rotating in the second, clockwise direction about longitudinal axis "A-A" in response to the transverse translation of rack 718 with respect to longitudinal axis "A-A" in the direction given by arrow "P." As such, trigger 710 is returned to the starting position but shaft 710 is not rotated clockwise about longitudinal axis "A-A" thereby undoing the prior operation.

Figure 8A:
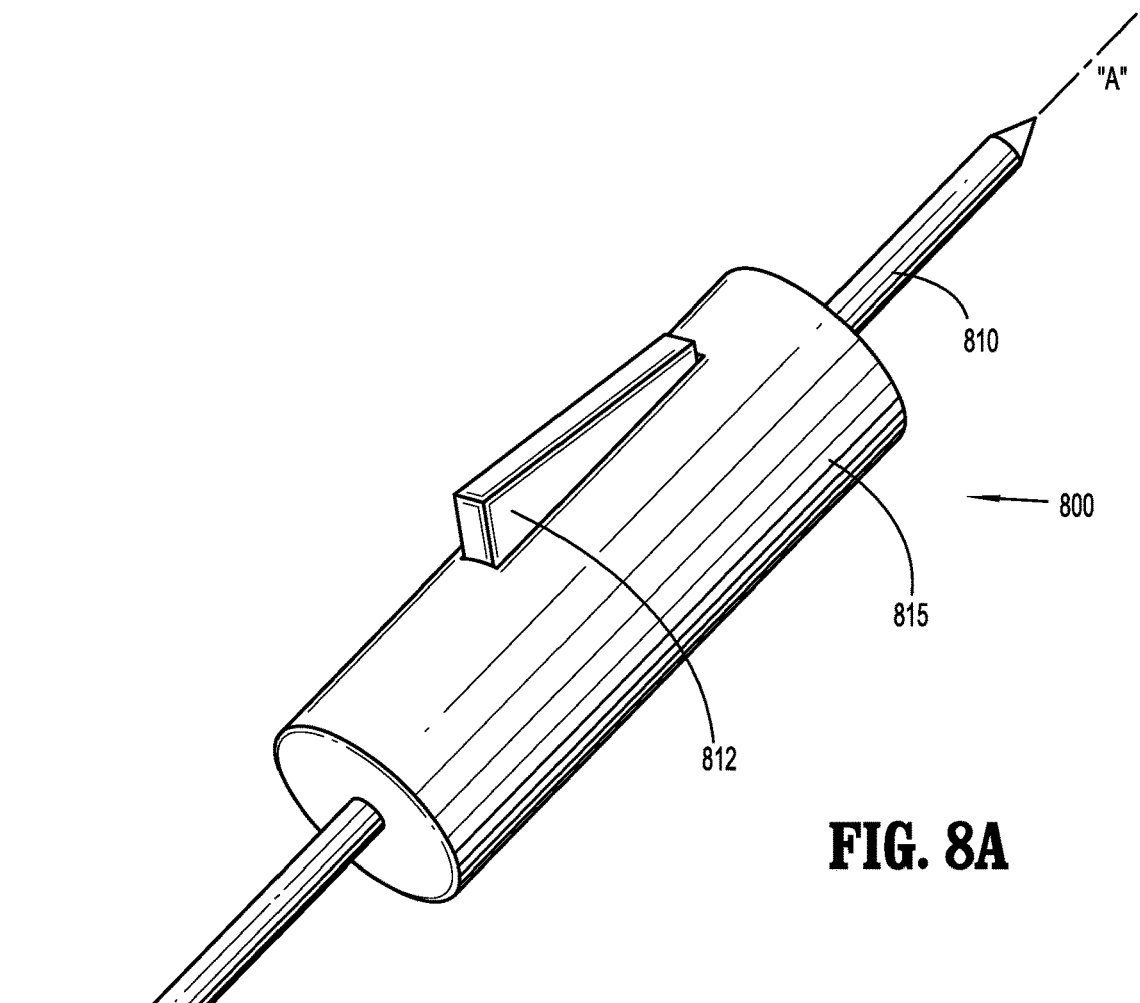
FIG. 8A is a perspective view of a manual retraction tool in accordance with another embodiment of the present disclosure.
Figure 8B:
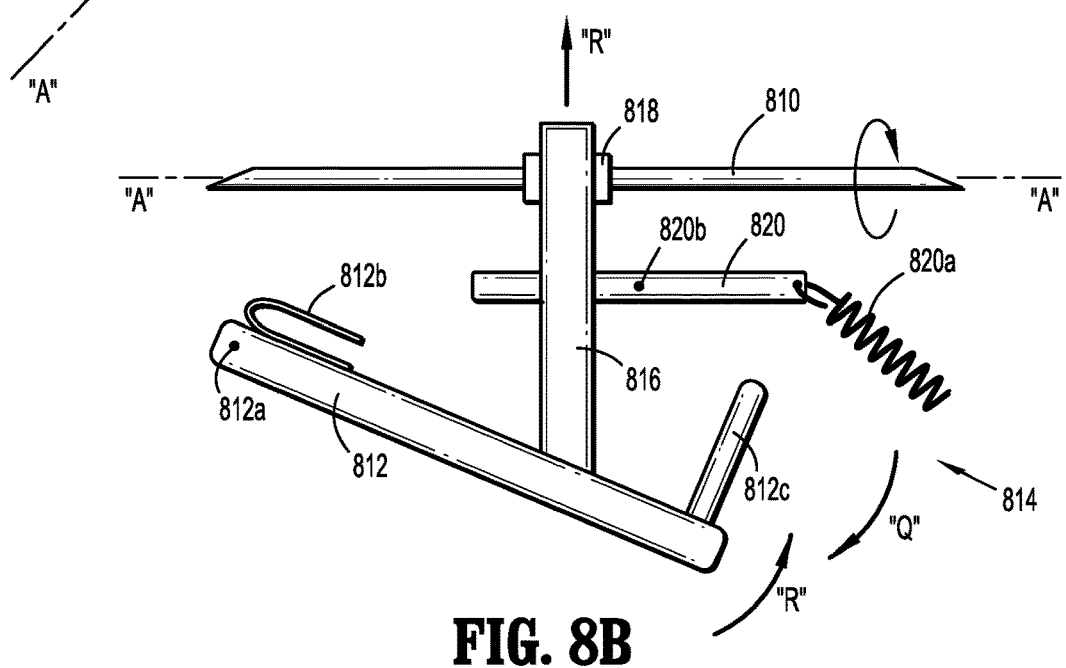
FIG. 8B is a perspective view of the manual retraction tool according to FIG. 8A with the housing removed in a first position.
Figure 8C:
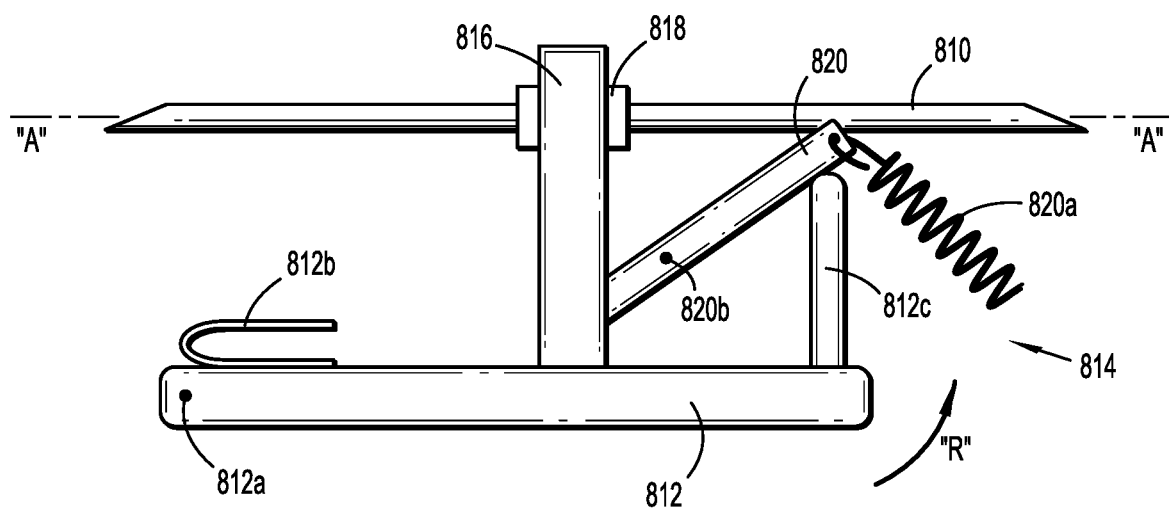
FIG. 8C is a perspective view of the manual retraction tool according to FIG. 8A with the housing removed in a second position.

Turning now to FIGS. 8A to 8C, an embodiment of a manual retraction tool 800 for use with an electromechanical surgical device, such as the one described above, is shown. Manual retraction tool 800 is similar to manual retraction tool 700 and will therefore only be described to the extent necessary to highlight and describe differences therebetween. Manual retraction tool 800 includes a shaft 810, a trigger 812, a ratchet assembly 814, and a housing 815 enclosing at least a portion of shaft 810 and ratchet assembly 814.

Trigger 812 includes a pivot 812*a* about which trigger 812 rotates relative to housing 815 between a first position (see FIG. 8B) and a second position (see FIG. 8C). Trigger 812 is acted on by a biasing member, such as, for example, spring 812*b*. Spring 812*b* is resiliently biased to the starting position in a direction given by arrow "Q." Trigger 812 also includes an arm 812*c* configured to translate transversely about longitudinal axis "A-A" with respect to housing 815 when trigger 812 is actuated.

As shown in FIGS. 8B and 8C, ratchet assembly 814 includes a rack 816, a ratchet wheel 818 fixed to shaft 810, and a shelf 820 located adjacent rack 816. Similar to rack 716 and ratchet wheel 718 of ratchet assembly 714, rack 816 and ratchet wheel 818 of ratchet assembly 814 each include a plurality of teeth (not shown) configured to engage the other plurality of teeth (not shown) to convert the transverse translation of rack 816 about longitudinal axis "A-A" with respect to housing 815 into a clockwise rotation of ratchet wheel 818 about longitudinal axis "A-A" with respect to housing 815 in a first direction.

In a first position as shown in FIG. 8B, a shelf 820 of housing 815 is located adjacent rack 816. Shelf 820 is resiliently biased to this position by a biasing member, such as, for example, spring 820*a*. When shelf 820 of housing 815 is in the first position, rack 816 is spaced apart from ratchet wheel 818. In this configuration, rack 816 is unable to engage ratchet wheel 818 to rotate ratchet wheel 818 when rack 816 is translated. It is contemplated that having a hard restraint, such as, for example, shelf 820, enhances the resistance of rack 816 disengaging from the ratchet wheel 818.

In a second position as shown in FIG. 8C, shelf 820 is rotated by arm 812*c* of trigger 812 when trigger 812 is rotated about pivot 812*a* in a direction given by an arrow "R." Shelf 820 rotates about a pivot 820*b* with respect to shaft 810 such that shelf 820 is no longer adjacent rack 816. Without the hard restraint on rack 816, rack 816 engages ratchet wheel 818 as it translates transversely about the longitudinal axis "A-A" to rotate ratchet wheel 818 in the first, clockwise direction about longitudinal axis "A-A." As a result, shaft 810 also rotates about longitudinal axis "A-A" with respect to housing 814 in the first direction.

In use, when trigger 812 is actuated, trigger 812 rotates about pivot 812*a* with respect to housing 814. As trigger 812 is rotated, arm 812*c* transversely translates with respect to longitudinal axis "A-A" in a direction given by the arrow "R." When arm 812*c* contacts shelf 820 and continues to translate in the direction given by arrow "R," arm 812*c* engages shelf 820 to rotate shelf 820 about pivot 820*b* relative to housing 814 in the direction given by "R." When shelf 820 is rotated such that it is no longer adjacent rack 816, the plurality of teeth (not shown) of rack 816 engages the plurality of teeth (not shown) of ratchet wheel 818. At the same time, rack 816 is also translating transversely about the longitudinal axis "A-A" with respect to housing 814 in the direction of arrow "R." The engagement between rack 816 and ratchet wheel 818 converts the translation of rack 816 to a rotation of ratchet wheel 818 about longitudinal axis "A-A" with respect to housing 814 in the first direction. Since ratchet wheel 818 is fixed to shaft 810, the rotation of the ratchet wheel 818 is directly converted to rotation of shaft 810 about longitudinal axis "A-A" with respect to housing 814. Similar to manual retraction tool 700, depending on which end of shaft 810 is inserted into adapter assembly 200 of electromechanical surgical device 100, electromechanical surgical device 100 is either manually retracted or manually fired.

When trigger 812 is released, spring 812*b* urges trigger 812 back to the starting position in the direction given by arrow "Q." During the return stroke of trigger 812, arm 812*c* spaces apart from shelf 820 and spring 820*a* urges shelf 820 back to its starting position adjacent rack 816. At this point, rack 816 disengages from ratchet wheel 818 and as such, the translation of rack 816 back to the starting position given by arrow "Q" does not convert into a counter-clockwise rotation of ratchet wheel 818 about longitudinal axis "A-A" in a second direction, thereby undoing or reversing the prior operation.

Turning now to FIGS. 9A to 9E, an embodiment of a manual retraction tool 900 for use with an electromechanical surgical device, such as the one described above is shown. Manual retraction tool 900 is similar to manual retraction tool 700 and will therefore only be described to the extent necessary to highlight and describe differences therebetween. Manual retraction tool 900 includes a shaft 910, a trigger 912, a ratchet assembly 914, and a housing 916 enclosing at least a portion of shaft 910 and ratchet assembly 914.

Figure 9A:
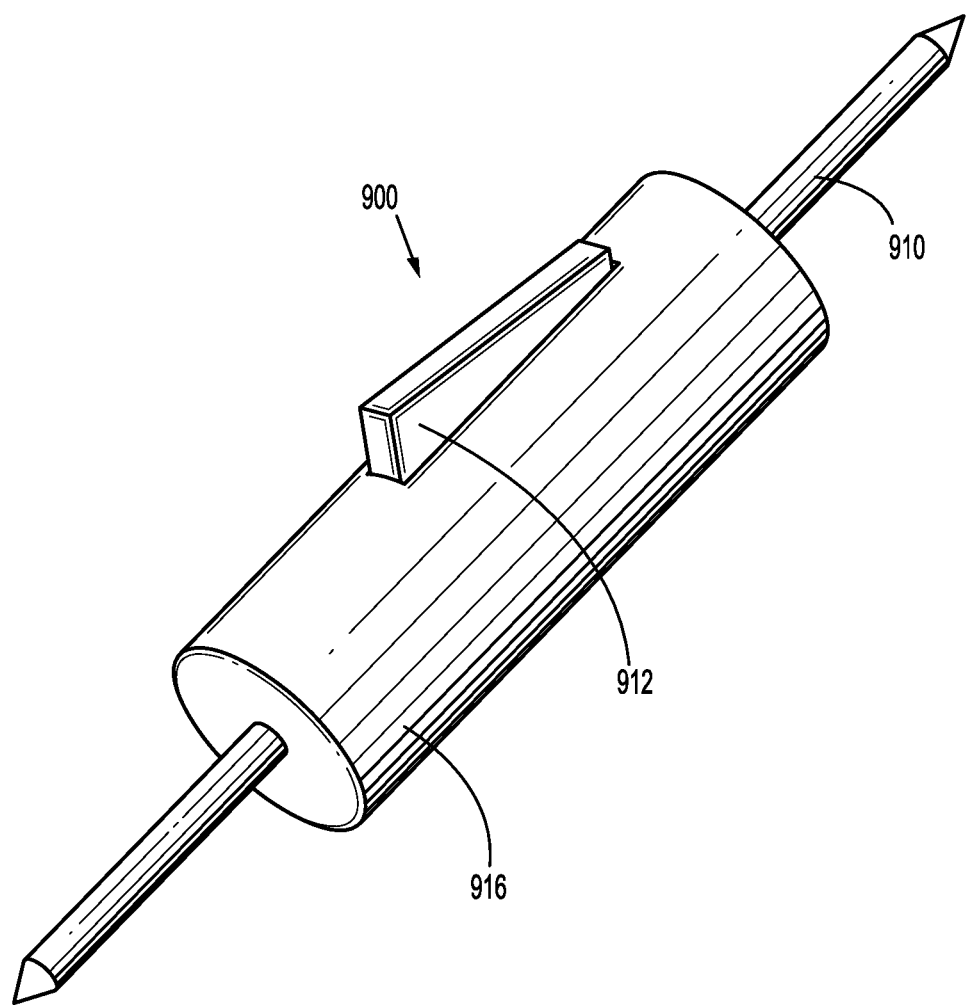
FIG. 9A is a perspective view of a manual retraction tool in accordance with another embodiment of the present disclosure.
Figure 9B:
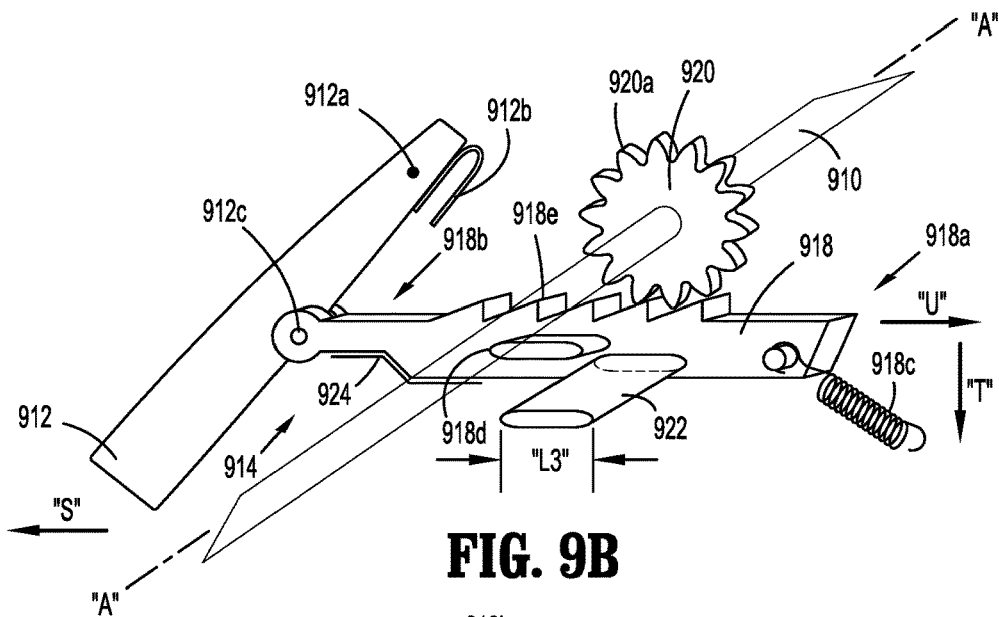
FIG. 9B is a perspective view of the manual retraction tool according to FIG. 9A with the housing removed and shown in a first position.
Figure 9C:
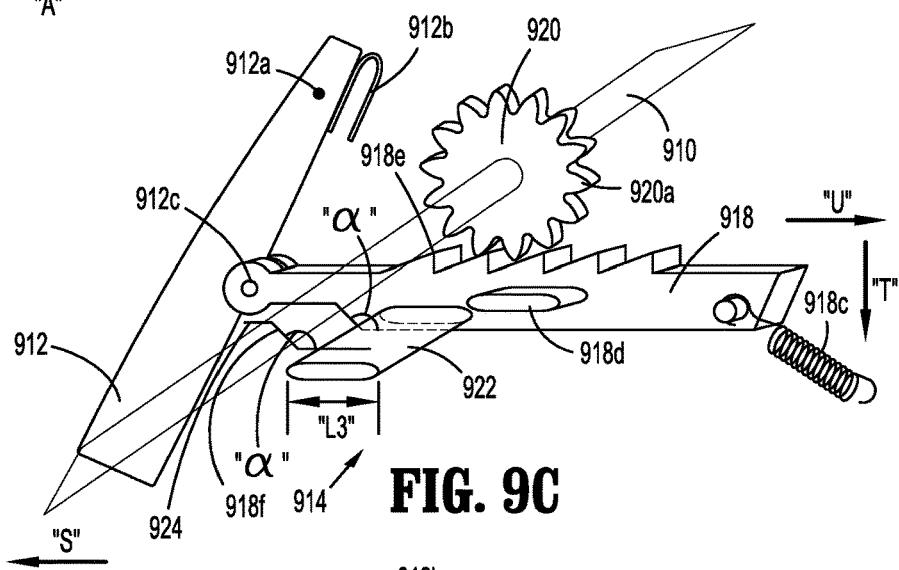
FIG. 9C is a perspective view of the manual retraction tool according to FIG. 9A with the housing removed and shown in an intermediate position.
Figure 9D:
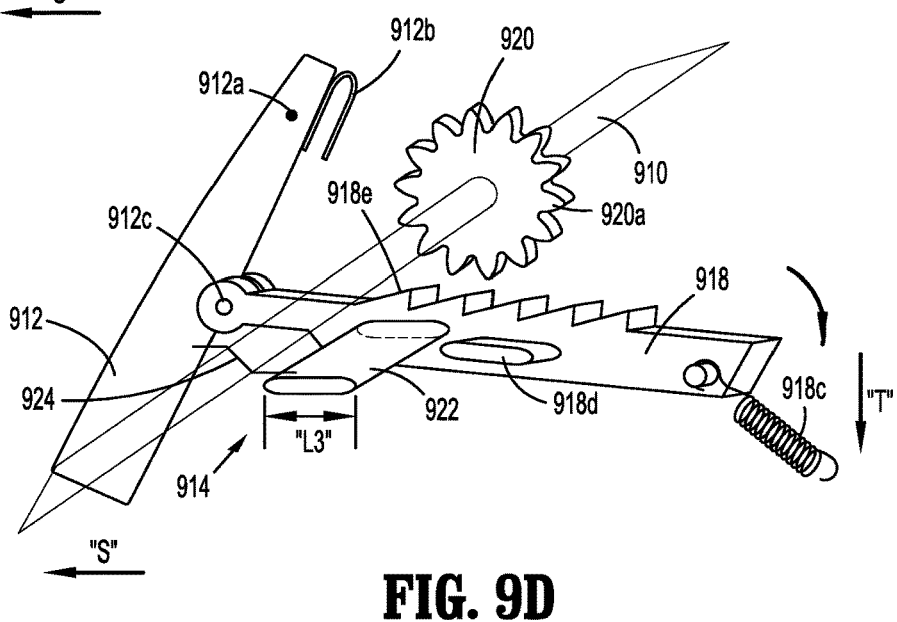
FIG. 9D is a perspective view of the manual retraction tool according to FIG. 9A with the housing removed and shown in a second position.

Trigger 912 includes a pivot 912a about which trigger 912 rotates relative to housing 916 between a first position (see FIG. 9B) and a second position (see FIG. 9D). Trigger 912 is acted upon by a biasing member, such as, for example, spring 912b. Spring 912b is resiliently biased to the starting position in a direction given by arrow "S."

Ratchet assembly 914 includes a rack 918, a ratchet wheel 920 fixed to shaft 910. Rack 918 extends between a distal end 918a and a proximal end 918b. Distal end 918a of rack 918 is connected to a biasing member, such as for example, spring 918c and proximal end 918b is pivotably fixed to trigger 912 at pivot 912c. Spring 918c is resiliently biased to urge rack 918 in a direction given by arrow "T." Rack 918 also includes a protrusion, such as, for example, shoulder 918d extending therefrom. Similar to the embodiments in manual retraction tools 700 and 800, rack 918 and ratchet wheel 920 of manual retraction tool 900 each include a plurality of teeth 918e and 920a, respectively, configured to engage one another to convert the transverse translation of rack 918 with respect to longitudinal axis "A-A" in a direction given by arrow "U" into rotation of ratchet wheel 920 about longitudinal axis "A-A" with respect to housing 916 in a first, counter clockwise direction.

Housing 916 includes an internal structure, such as, for example, a ledge 922 configured for supporting shoulder 918d of rack 918 when trigger 912 is actuated. When shoulder 918d of rack 918 rides on ledge 922, rack 918 is engaged with ratchet wheel 920 as described above. In embodiments when ledge 922 defines a length "L3," shoulder 918d rides ledge 922 for a distance of length "L3" after which the bias of spring 918c pulls rack 918 down in the direction given by arrow "T" (see FIG. 9D).

Figure 9E:
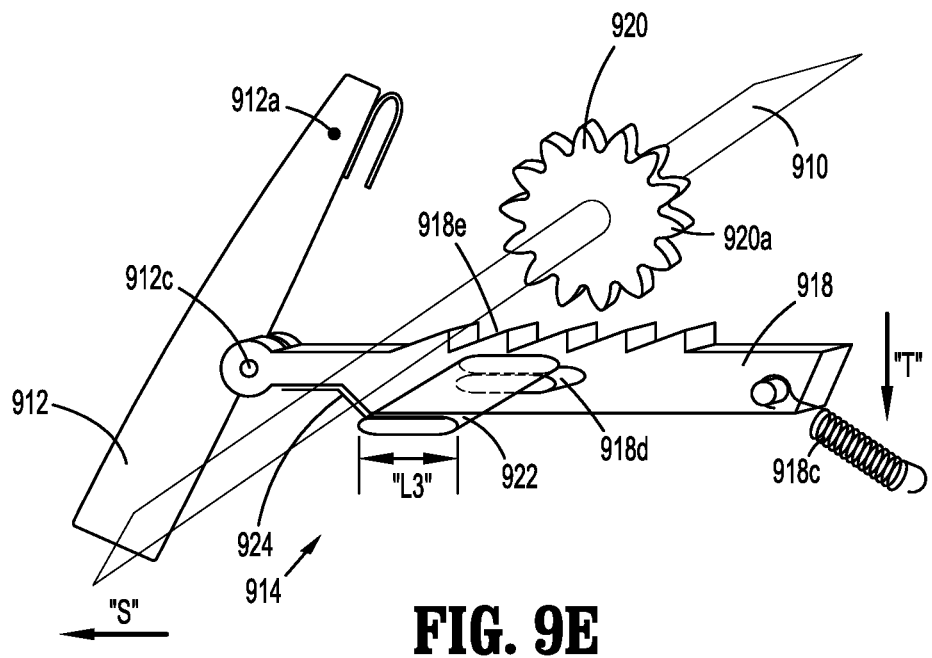
FIG. 9E is a perspective view of the manual retraction tool according to FIG. 9A with the housing removed and shown in an intermediate position.
Figure 9F:
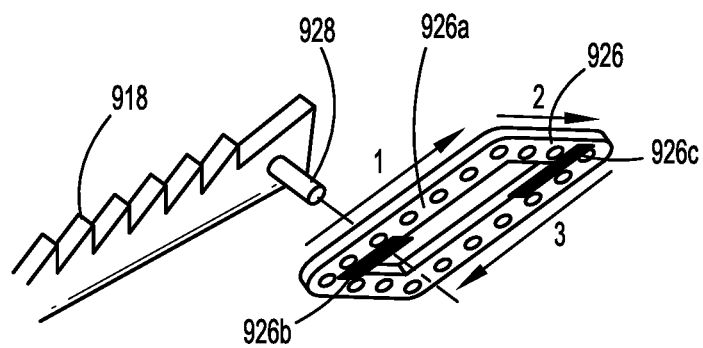
FIG. 9F is a perspective view of an alternative embodiment of the manual retraction tool of FIG. 9A.

In embodiments, ledge 922 of housing 916 may be substituted for a body track 926 as shown in FIG. 9F. In this embodiment, rack 918 includes a protrusion, such as, for example, a post 928 extending therefrom. Post 928 is configured to translate along a rail 926a of body track 926. Similar to the engagement between shoulder 918d of rack 918 and ledge 922 of housing 916, the engagement between post 928 of rack 918 and body track 926 facilitates the engagement between the plurality of teeth 918e and 920a of rack 918 and ratchet wheel 920, respectively, to convert the transverse translation of rack 918 with respect to longitudinal axis "A-A" in the direction given by "U" into rotation of ratchet wheel 920 about longitudinal axis "A-A" with respect to housing 916. Continuing with FIG. 9F, rail 926a of body track 926 includes a first biasing member, such as, for example, a leaf spring 926b and a second biasing member, such as, for example, a leaf spring 926c. Leaf springs 926b and 926c are resiliently biased to prevent post 928 of rack 918 from translating in a reverse direction to a direction shown by arrows 1, 2, and 3. In particular, leaf springs 926b and 926c act as one way trap doors which ensures that trigger 912 will return to the start position shown in FIG. 9B.

Turning back to FIGS. 9A-9E, housing 916 also includes a ramp 924 configured to engage proximal end 918b of rack 918. In particular, an angled portion 918f of the proximal end 918b of rack 918 is configured to slide up ramp 924 from the position shown in FIG. 9E back to the starting position as shown in FIG. 9B. In embodiments, it is contemplated that an angle "α" of ramp 924 is equal to an angle "α'" of angled portion 918f of the proximal end 918b of rack 918 (see FIG. 9C). However, it is also contemplated that in embodiments, the angle "α" of the ramp 924 is greater than the angle "α'" of angled portion 918f of the proximal end 918b of rack 918.

In use, when trigger 912 is actuated, trigger 912 rotates about pivot 912a relative to housing 916 to translate rack 918 transversely with respect to longitudinal axis "A-A" in the direction given by "U." As rack 918 translates in the direction given by "U," shoulder 918d of rack 918 rides on ledge 922 of housing 916 for a distance "L3." As detailed above, when shoulder 918d of rack 918 is engaged with ledge 922 of housing 916, the plurality of teeth 918e of rack 918 engages the plurality of teeth 920a of the ratchet wheel 920. In doing so, the transverse translation of rack 918 with respect to longitudinal axis "A-A" in the direction given by "R" is converted into rotation of ratchet wheel 920 about longitudinal axis "A-A" with respect to housing 916. Since ratchet wheel 920 is fixed to shaft 910, the rotation of the ratchet wheel 920 is directly converted to rotation of shaft 910 about longitudinal axis "A-A" with respect to housing 916. Similar to manual retraction tools 700 and 800, depending on which end of shaft 910 is inserted into adapter assembly 200 of electromechanical surgical device 100, electromechanical surgical device 100 is either manually retracted or manually fired.

As shown in FIG. 9D, after shoulder 918d has traversed the distance "L3" of ledge 922 and trigger 912 is released, spring 918c urges rack 918 in the direction given by arrow "T." At the same time, spring 912b urges trigger 912 back to the starting position in the direction given by arrow "S" (see FIG. 9E). During the return stroke of trigger 912, when shoulder 918d of rack 918 is no longer supported by ledge 922 of housing 916, rack 918 disengages from ratchet wheel 920. As such, the translation of rack 918 back to the starting position given by arrow "S" does not convert into counter-clockwise rotation of ratchet wheel 920 about longitudinal axis "A-A" thereby undoing or reversing the prior operation.

Figure 10A:
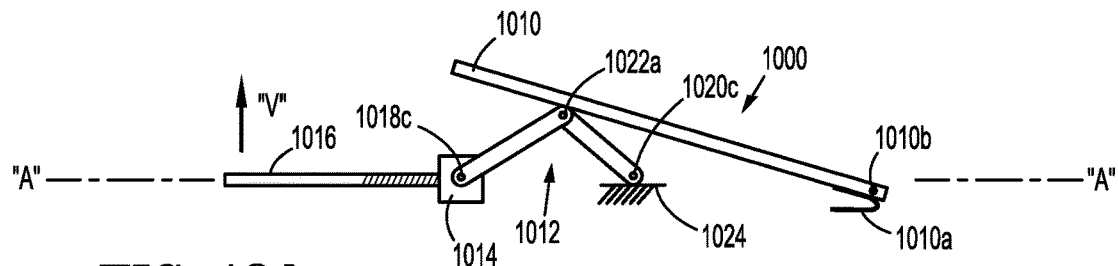
FIG. 10A a side view of a manual retraction tool in accordance with another embodiment of the present disclosure.

Turning now to FIGS. 10A to 10D, an embodiment of a manual retraction tool 1000 for use with an electromechanical surgical device, such as the one described above is shown. Manual retraction tool 1000 is similar to manual retraction tool 400 and will therefore only be described to the extent necessary to highlight and describe differences therebetween. Manual retraction tool 1000 includes a trigger 1010 which is configured to engage a linkage assembly 1012. As shown in FIG. 10A, the linkage assembly 1012 is coupled to a nut 1014 supporting a shaft 1016. Similar to manual retraction tool 400, when nut 1014 is engaged by linkage assembly 1012, shaft 1016 rotates about longitudinal axis "A-A" to either retract or fire electromechanical surgical device 100. Though not explicitly shown, manual retraction tool 1000 is partially contained in a housing similar to housing 916 of manual retraction tool 900.

Trigger 1010 is spring loaded with a biasing member, for example, a spring 1010a. Spring 1010a is resiliently biased to a starting position given by an arrow "V." However, upon actuation, trigger 1010 is rotatable about a pivot 1010b with respect to longitudinal axis "A-A."

Figure 10B:
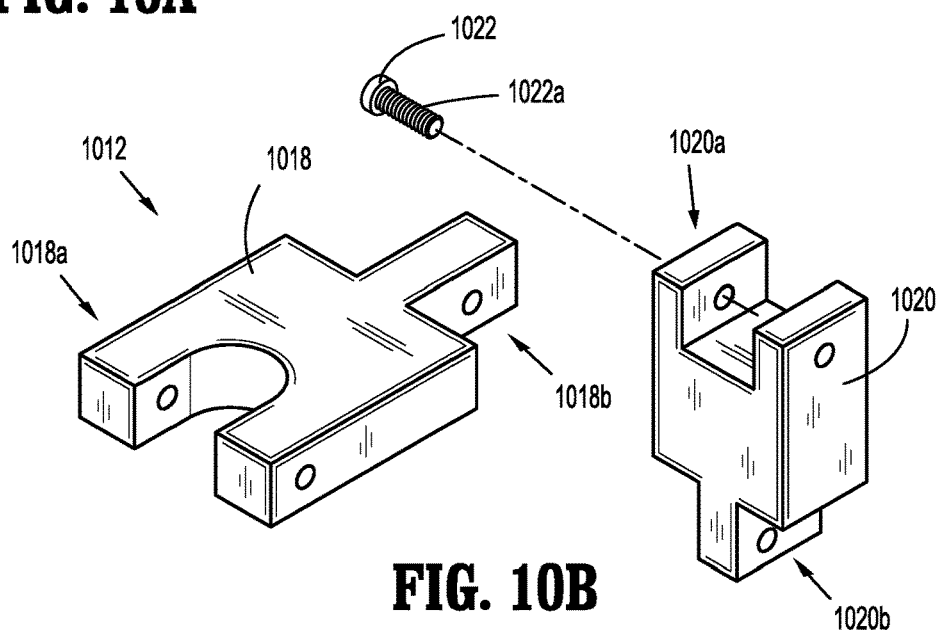
FIG. 10B is a perspective view of a linkage assembly of the manual retraction tool according to FIG. 10A.

Trigger 1010 is operatively coupled to linkage assembly 1012. As shown in FIG. 10B, linkage assembly 1012 includes a first link 1018 and a second link 1020. First link 1018 extends between a distal portion 1018a and a proximal portion 1018b. Similarly, second link 1020 extends between a distal portion 1020a and a proximal portion 1020b. In embodiments, proximal portion 1018b of first link 1018 is pivotably coupled to the distal portion 1020a of second link 1020 with fastener 1022 at a pivot 1022a (see FIG. 10A). Similarly, distal portion 1018a of first link 1018 is pivotably coupled to nut 1014 at a pivot 1018c and proximal portion 1020b of second link 1020 is pivotably coupled to an internal structure of the housing (not shown), such as, for example, a ledge 1024 at a pivot 1020c (see FIG. 10A).

Figure 10C:
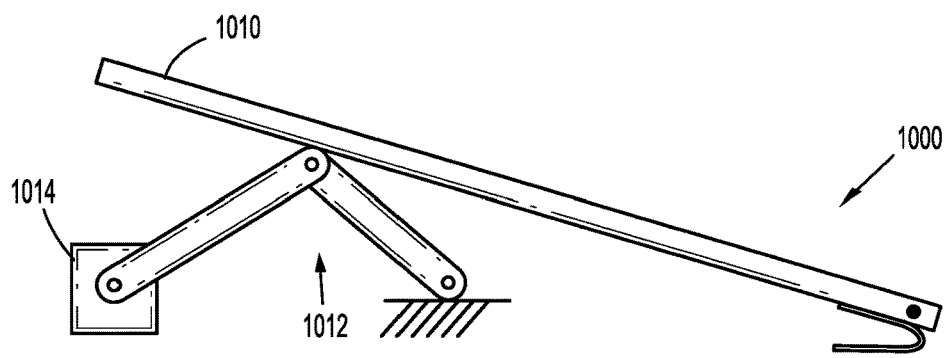
FIG. 10C is a side view of the manual retraction tool of FIG. 10A illustrating the tool in a first position.
Figure 10D:
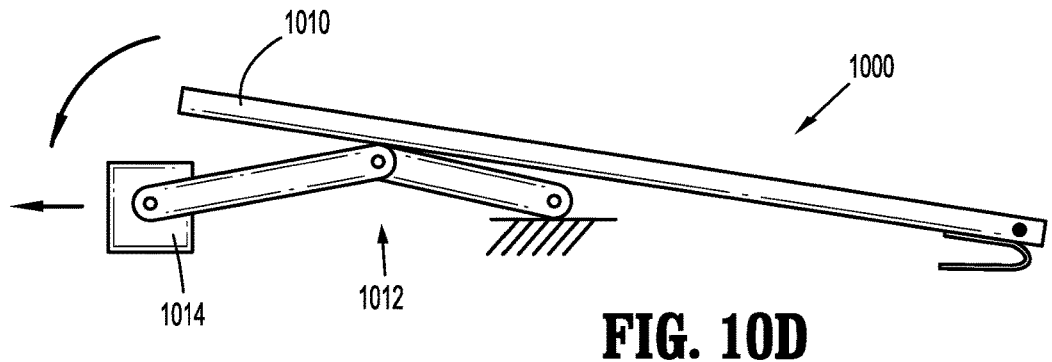
FIG. 10D is a side view of the manual retraction tool of FIG. 10A illustrating the tool in a second position.

In embodiments, fastener 1022 is spring loaded with a biasing member, such as, for example, a spring 1022d. It is contemplated that spring 1022a of fastener 1022 is resiliently biased to the starting position given by arrow "V." In use, when trigger 1010 is in the first starting position as shown in FIG. 10C, the bias of spring 1022a also urges linkage assembly 1012 to the starting position given by arrow "V." When trigger 1010 is actuated to a second position as shown in FIG. 10D, trigger 1010 compresses linkage assembly 1012 against the bias of spring 1022a of fastener 1022. In particular, the first link 1018 of linkage assembly 1012 is translated along the longitudinal axis "A-A" in a direction of arrow "W" to rotate shaft 1016 about longitudinal axis "A-A" to either retract or fire electromechanical surgical device 100.

In alternative embodiments, linkage assembly 1012 is pivotably fixed to trigger 1010 at the pivot 1022a. In use, when trigger 1010 is in the first, starting position under the bias of spring 1010a, linkage assembly 1012 is also in the starting position as shown in FIG. 10C. When trigger 1010 is actuated to the second position as shown in FIG. 10D, trigger 1010 compresses linkage assembly 1012 such that the first link 1018 of linkage assembly 1012 is translated along the longitudinal axis "A-A" in a direction of arrow "W" to rotate shaft 1016 about longitudinal axis "A-A" to either retract or fire electromechanical surgical device 100. When trigger 1010 is released, the bias of spring 1010a urges trigger 1010 back to the first, starting position given by arrow "V." As a result, linkage assembly 1012 is also urged back to the starting position. It is contemplated that manual retraction tool 1000 includes a ratchet assembly (not shown) similar to ratchet assembly 428 of manual retraction tool 400 (see FIG. 4). As detailed with reference to manual retraction tool 400, ratchet assembly 428 prevents shaft 414 from rotating in the opposite direction about longitudinal axis "A-A" when trigger 410 returns to the starting position. Similarly, when trigger is returned back to the starting position given by arrow "V," the ratchet assembly (not shown) of manual retraction tool 1000 prevents nut 1014 from rotating shaft 1016 in the opposite direction about longitudinal axis "A-A" with the release of trigger 1010.

Turning now to FIGS. 11A to 11E, an embodiment of a manual retraction tool 1100 for use with an electromechanical surgical device, such as the one described above is shown. Manual retraction tool 1100 is similar to manual retraction tool 600 detailed above and will therefore only be described to the extent necessary to highlight its differences. Manual retraction tool 1100 includes a housing 1120 configured to be connected to adapter assembly 200. In particular, a clinician can attach housing 1120 to adapter assembly 200 via attachment/detachment button 214. This enables the clinician to use manual retraction tool 1100 without having to manually hold it in place against adapter assembly 200.

Figure 11A:
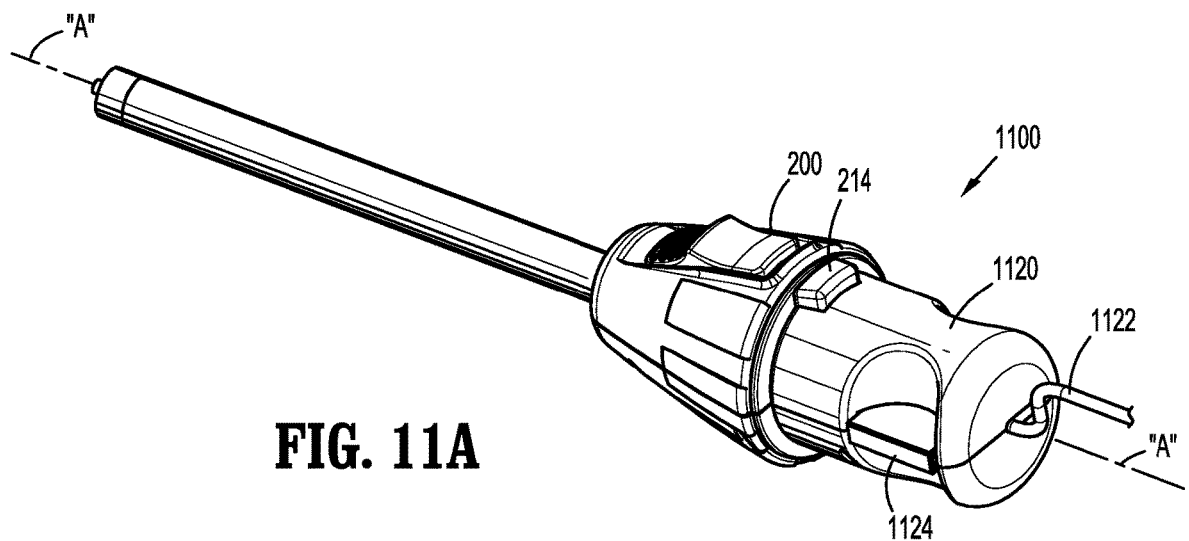
FIG. 11A is a perspective view of a manual retraction tool in accordance with another embodiment of the present disclosure.
Figure 11B:
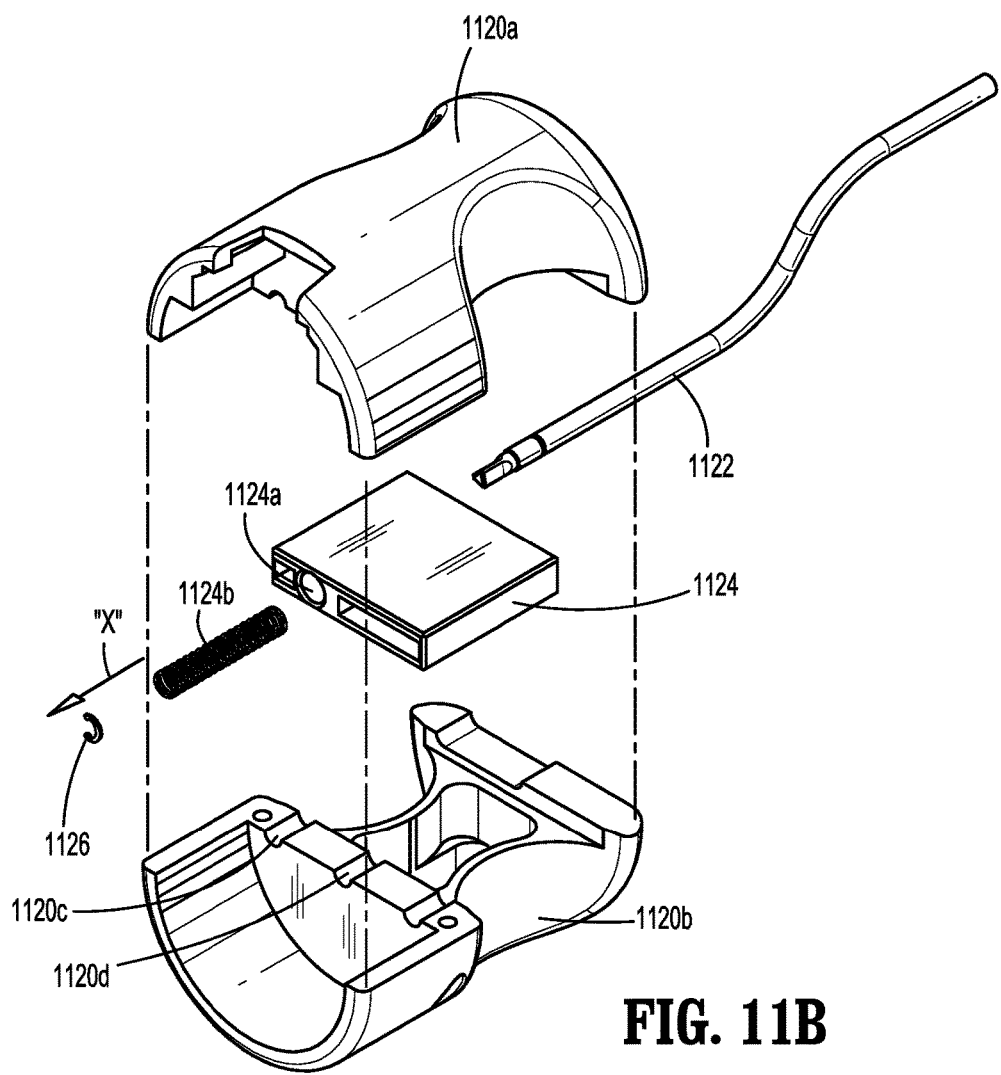
FIG. 11B is an exploded perspective view of the manual retraction tool of FIG. 11A.

As shown in FIG. 11B, housing 1120 includes a top or first-half portion 1120a and a bottom or a second-half portion 1120b. Top portion 1120a and bottom portion 1120b together define a clamshell configuration for housing 1120. Housing 1120 also defines a first through-hole 1120c and a second through-hole 1120d, each extending along the longitudinal axis "A-A." First through-hole 1120c and second through-hole 1120d are configured to locate a crank 1122 of manual retraction tool 1100 to articulate and/or fire/retract electromechanical surgical device 100, as detailed below.

To that end, manual retraction tool 1100 includes a slider 1124 configured to alternate the operation of manual retraction tool 1100 between articulating and/or firing/retracting of electromechanical surgical device 100. Slider 1124 is disposed within a track 1120e of the housing 1120 and is configured to slide along track 1120e in a direction transverse to the longitudinal axis "A-A" between the articulation position and the firing/retracting position. Slider 1124 includes a through-hole 1124a configured for locating crank 1122. When slider 1124 is in the articulating position, through-hole 1124a of slider 1124 is aligned with the first through-hole 1120c of housing 1120, as shown in FIG. 11E. Alternatively, when slider 1124 is in the firing/retracting position, through-hole 1124a of slider 1124 is aligned with the second through-hole 1120d of housing 1120, as shown in FIG. 11D.

As shown in FIG. 11C, crank 1122 extends between a distal portion 1122a and a proximal portion 1122c and includes a bent portion 1122b therebetween. Distal portion 1122a of crank 1122 is disposed within through-hole 1124a of slider 1124. In embodiments, distal portion 1122a of crank 1122 includes a distal tip 1122d having a trilobe configuration. However, it is contemplated that distal tip 1122d may include any suitable configuration. As shown in FIG. 11B, distal portion 1122a of crank 1122 also includes a groove 1122e for locating a retaining ring 1126. Retaining ring 1126 is dimensioned to prevent distal translation of crank 1122 past a distal wall 1120f of housing 1120. Continuing with FIG. 11B, through-hole 1124a of slider 1124 houses a biasing member, such as, for example, a spring 1124b. Spring 1124b is resiliently biased to urge the distal portion 1122a of crank 1122 in a distal direction given by arrow "X" to keep manual retraction tool 1100 engaged to electromechanical surgical device 100.

In use, manual retraction tool 1100 is attached to adapter assembly 200 of electromechanical surgical device 100 via attachment/detachment button 214. When articulating adapter assembly 200 of electromechanical surgical device 100, slider 1124 is positioned in the articulation position as shown in FIG. 11E. At that time, distal portion 1122a of crank 1122 extends through through-hole 1124a of slider 1124 and first through-hole 1120c housing 1120 such that distal tip 1122d engages a corresponding driver on adapter assembly 200. To operate manual retraction tool 1100 to articulate adapter assembly 200 of electromechanical surgical device 100, proximal portion 1122b of crank 1122 is rotated about longitudinal axis "A-A."

When firing/retracting electromechanical surgical device 100, proximal portion 1122b of crank 1122 is pulled against the bias of spring 1124b to translate crank 1124 proximally along longitudinal axis "A-A" until distal tip 1122d is no longer in the first through-hole 1120c of housing 1120. At this point, slider 1124 is translated transversely about longitudinal axis "A-A" until through-hole 1124a of slider 1124 is aligned with second through-hole 1120d of housing 1120. Once crank 1122 is released, spring 1124b urges distal portion 1122a of crank 1122 in the direction given by arrow "X" such that distal tip 1122d engages a corresponding driver of adapter assembly 200. To operate manual retraction tool 1100 to fire/retract electromechanical surgical device 100, proximal portion 1122b of crank 1122 is rotated about longitudinal axis "A-A."

With reference to FIGS. 12A-12C, a manual retraction tool 1300, which may include the various manual retraction tools 400, 500, 600, 700, 800, 900, 100, or 1100, detailed in the present disclosure is also configured to operate with an adapter assembly 2200 of an electromechanical surgical device 2000 in the form of a powered handheld electromechanical instrument, specifically, an End-to-End Anastomosis (EEA) device.

Electromechanical surgical device 2000 includes a handle housing 2102 configured for selective connection with the adapter assembly 2200. Handle housing 2102 and adapter assembly 2200 of electromechanical surgical device 2000 are substantially similar to handle housing 102 and adapter assembly 200 of electromechanical surgical 100 device detailed above.

Adapter assembly 2200 is configured for selective connection with an extension assembly 2020. The extension assembly 2020 is configured for selective connection with a tool assembly or end effector 2030, which may, in exemplary embodiments, include a loading unit 2040 and an anvil assembly 2050, for applying a circular array of staples (not shown) to tissue (not shown).

Handle housing 2102 includes rotatable drive connectors (not shown) similar to rotatable drive connectors 106, 108, 110 of handle housing 102 of electromechanical surgical 100. When adapter assembly 2200 is mated to handle housing 2102, the rotatable drive connectors (not shown) of handle housing 2102 is coupled with corresponding rotatable connector sleeves 2206, 2208, 2210 of a drive coupling assembly 2212 of adapter assembly 2200, to enable rotational forces to be independently transmitted via each of the three respective connector interfaces.

Adapter assembly 2200 includes a plurality of force/rotation transmitting/converting assemblies disposed therein. Each force/rotation transmitting/converting assembly is configured and adapted to transmit/convert a speed/force of rotation (e.g., increase or decrease) of the rotatable drive connectors (not shown) of handle housing 2102 before transmission of such rotational speed/force to end effector 2030.

For a detailed description of the construction and operation of exemplary electromechanical surgical devices 2000, adapter assemblies 2200, and end effectors 2030, reference may be made to U.S. Provisional Patent Application No. 62/197,710, filed on Jul. 28, 2015, the entire content of which is incorporated herein by reference.

As noted above, manual retraction tool 1300 may include the various manual retraction tools 400, 500, 600, 700, 800, 900, 100, or 1100, detailed in the present disclosure. Accordingly, the use and operation of manual retraction tool 1300 will be substantially similar to the manual retraction tools detailed above. Though not specifically shown in FIG. 12C, generally, manual retraction tool 1300 will include a housing, a rotatable shaft disposed within the housing, a rotation or actuation mechanism configured to rotate the rotatable shaft, and a trigger configured to engage the actuation mechanism. In use, an end portion of the rotatable shaft is inserted into one of the rotatable connector sleeves 2206, 2208, 2210 of drive coupling assembly 2212 of adapter assembly 2200. The trigger is then actuated to engage the actuation mechanism to rotate the rotatable shaft. Depending on which end of the rotatable shaft that is inserted into the rotatable connector sleeves 2206, 2208, 2210 of drive coupling assembly 2212 of adapter assembly 2200, end effector 2030 is made to fire or retract.

Figure 13:
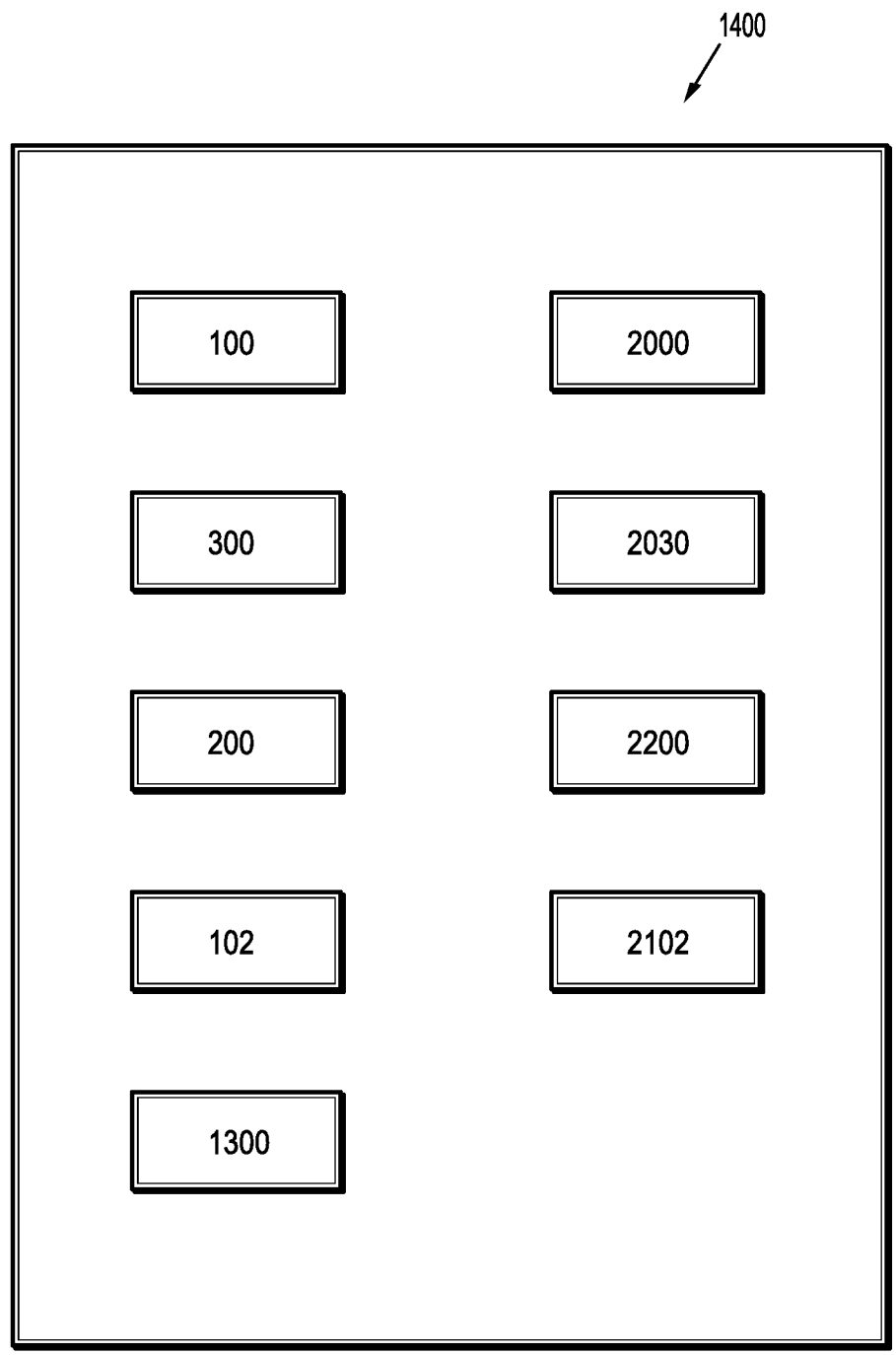
FIG. 13 is a kit including the electromechanical surgical device of FIG. 1, the electromechanical surgical device of FIG. 12A, the adapter assembly of FIG. 2, the adapter assembly of FIG. 12B, and the manual retraction tool of FIG. 12C.

With reference to FIG. 13, and also in accordance with the present disclosure, it is further contemplated that a surgical kit 1400 may be provided including electromechanical surgical device 100 having adapter assembly 200 configured for selective connection with loading unit 300 and electromechanical surgical device 2000 having adapter assembly 2200 configured for selective connection with end effector 2030. Kit 1400 may also include manual retraction tool 1300. As noted above, manual retraction tool 1300 may include any of the manual retraction tools 400, 500, 600, 700, 800, 900, 1000, or 1100. In some embodiments, kit 1400 may include one or both handle housings 102, 2102, as it is contemplated that either of handle housings 102, 2102 may work with adapter assemblies 200, 2200. Kit 1400 may also include instructions for the assembly, use, and post-use processing of electromechanical surgical devices 100, 2000 and manual retraction tool 1300. Kit 1400 may further include a package, container, or box configured to retain the components of kit 1400.

It will be understood that various modifications may be made to the embodiments disclosed herein. For example, the shape of a handle may be modified, e.g., to include grips, for ease of handling by a clinician. Therefore, the above description should not be construed as limiting, but merely as exemplifications of preferred embodiments. Those skilled in the art will envision other modifications within the scope and spirit of the claims appended thereto.

What is claimed is:

1. A manual retraction tool for use with a surgical tool assembly of a surgical device, the manual retraction tool comprising:
   a housing configured for releasable attachment to a surgical tool assembly, the housing including a first through-hole configured for alignment with a first rotational connector of the surgical tool assembly, and a second through-hole configured for alignment with a second rotational connector of the surgical tool assembly;
   a crank at least partially supported in the housing, the crank including a distal portion dimensioned to be inserted into one of the first rotational connector of the surgical tool assembly or the second rotational connector of the surgical tool assembly at a time, wherein rotation of the crank is configured to effect rotation of one of the first rotational connector or the second rotational connector at a time; and
   a slider disposed within a track defined in the housing and configured to support the distal portion of the crank.

2. The manual retraction tool according to claim 1, wherein the slider is configured to slide along the track to align the distal portion of the crank with the first through-hole of the housing or the second through-hole of the housing.

3. The manual retraction tool according to claim 2, wherein the slider includes a slider through-hole configured for aligning the distal portion of the crank with the first through-hole of the housing or the second through-hole of the housing.

4. The manual retraction tool according to claim 3, wherein the distal portion of the crank defines a longitudinal axis, a portion of the crank is configured to rotate along the longitudinal axis, and the slider is configured to slide along the track in a direction perpendicular to the longitudinal axis.

5. The manual retraction tool according to claim 4, wherein the slider through-hole includes a biasing member configured to urge the crank in a distal direction.

6. The manual retraction tool according to claim 1, wherein the slider includes a slider through-hole configured for aligning the distal portion of the crank with the first through-hole of the housing or the second through-hole of the housing, and wherein the slider through-hole includes a biasing member configured to urge the crank in a distal direction.

7. The manual retraction tool according to claim 1, wherein a distal portion of the housing defines a clamshell configuration.

8. A manual retraction tool for use with a surgical tool assembly of a surgical device, the manual retraction tool comprising:
- a housing configured for releasable attachment to a surgical tool assembly, the housing including a first through-hole configured for alignment with a first rotational connector of the surgical tool assembly, and a second through-hole configured for alignment with a second rotational connector of the surgical tool assembly, the housing defining a track;
- a crank at least partially supported in the housing, the crank including a distal portion dimensioned to be inserted into one of the first rotational connector of the surgical tool assembly or the second rotational connector of the surgical tool assembly at a time, the distal portion of the crank defining a longitudinal axis, wherein rotation of the crank about the longitudinal axis is configured to effect rotation of one of the first rotational connector or the second rotational connector at a time; and
- a slider disposed within the track defined by the housing, wherein the slider is configured to slide along the track in a direction perpendicular to the longitudinal axis.

9. A manual retraction tool for use with a surgical tool assembly of a surgical device, the manual retraction tool comprising:
- a housing configured for releasable attachment to a surgical tool assembly, the housing including a first through-hole configured for alignment with a first rotational connector of the surgical tool assembly, and a second through-hole configured for alignment with a second rotational connector of the surgical tool assembly, a distal portion of the housing defining a clamshell configuration;
- a crank at least partially supported in the housing and dimensioned to be inserted into one of the first rotational connector of the surgical tool assembly or the second rotational connector of the surgical tool assembly at a time, wherein rotation of the crank is configured to effect rotation of one of the first rotational connector or the second rotational connector at a time; and
- a slider disposed within a track defined in the housing and configured to support a portion of the crank.

* * * * *